US011400126B2

(12) United States Patent
Portugal Cohen et al.

(10) Patent No.: US 11,400,126 B2
(45) Date of Patent: Aug. 2, 2022

(54) COMPOSITIONS COMPRISING DEAD SEA EXTRACT AND AN EXTRACT OF APPLE OF SODOM AND USES THEREOF

(71) Applicant: AHAVA—DEAD SEA LABORATORIES LTD., Lod (IL)

(72) Inventors: Meital Portugal Cohen, Jerusalem (IL); Zeevi Maor, Dead Sea D.N Arvot Hayarden (IL); Eliran Ish-Shalom, Kibbutz Tel Yosef (IL); Dror Cohen, Kibbutz Ein Gedi (IL)

(73) Assignee: AHAVA—DEAD SEA LABORATORIES LTD., Lod (IL)

( * ) Notice: Subject to any disclaimer, the term of this patent is extended or adjusted under 35 U.S.C. 154(b) by 43 days.

(21) Appl. No.: 15/733,319

(22) PCT Filed: Dec. 26, 2018

(86) PCT No.: PCT/IL2018/051391
§ 371 (c)(1),
(2) Date: Jun. 25, 2020

(87) PCT Pub. No.: WO2019/130301
PCT Pub. Date: Jul. 4, 2019

(65) Prior Publication Data
US 2021/0393721 A1  Dec. 23, 2021

(30) Foreign Application Priority Data

Dec. 28, 2017  (IL) .......................................... 256648

(51) Int. Cl.
*A61K 36/00* (2006.01)
*A61K 36/24* (2006.01)
*A61K 8/9789* (2017.01)
*A61P 17/02* (2006.01)
*A61K 8/96* (2006.01)
*A61K 35/08* (2015.01)
*A61Q 19/02* (2006.01)
*A61Q 19/08* (2006.01)
*A61K 9/00* (2006.01)

(52) U.S. Cl.
CPC .............. *A61K 36/24* (2013.01); *A61K 8/965* (2013.01); *A61K 8/9789* (2017.08); *A61K 35/08* (2013.01); *A61P 17/02* (2018.01); *A61Q 19/02* (2013.01); *A61Q 19/08* (2013.01); *A61K 9/0014* (2013.01)

(58) Field of Classification Search
CPC .......... A61P 17/02; A61Q 19/08; A61K 35/08
See application file for complete search history.

(56) References Cited

U.S. PATENT DOCUMENTS

| | | | |
|---|---|---|---|
| 6,582,709 B1 * | 6/2003 | Maor | ........................ A61K 9/06 424/401 |
| 2006/0205679 A1 | 9/2006 | Streeper et al. | |
| 2013/0236571 A1 | 9/2013 | Magdassi et al. | |

FOREIGN PATENT DOCUMENTS

| | | |
|---|---|---|
| CA | 2 501 240 A1 | 4/2004 |
| EP | 2 174 648 A1 | 4/2010 |
| WO | 99/33443 A1 | 7/1999 |
| WO | 2004/032947 A1 | 4/2004 |
| WO | 2004/032948 A1 | 4/2004 |
| WO | 2005/099730 A1 | 10/2005 |
| WO | 2009/155497 A1 | 12/2009 |

OTHER PUBLICATIONS

Falguni et al., International Journal of Drug Discovery and Herbal Research (IJDDHR) (2012), No. October/December, pp. 493-498 (Year: 2012).*
Arya et al., "Antiinflammatory Efficacy of Extracts of Latex of Calotropis procera Against Different Mediators of Inflammation", Mediators of Inflammation 2005, 2005, vol. 4, pp. 228-232.
Azmir et al., "Techniques for extraction of bioactive compounds from plant materials: A review", Journal of Food Engineering, 2013, vol. 117, pp. 426-436.
Choedon et al., "Anticancer and cytotoxic properties of the latex of Calotropis procera in a transgenic mouse model of hepatocellular carcinoma", World J Gastroenterol, 2006, vol. 12, No. 16, pp. 2517-2522.
El-Bakry et al., "Production of Cardiac Glycosides from Calotropis Procera by Cell Suspension Cultures", Journal of Applied Sciences Research, 2011, vol. 7, No. 9, pp. 1375-1385.
GSEA—MSigDB-MSigDB Collections, 2018, Broad Institute, Inc., Massachusetts Institute of Technology, and Regents of the University of California, two pages, available online at: http://software.broadinstitute.org/gsea/msigdb/collections.jsp.
Halevy et al., "Dead sea bath salt for the treatment of psoriasis vulgaris: a double-blind controlled study", Journal of the European Academy of Dermatology and Venereology, 1997, vol. 9, pp. 237-242.
Mosemi, "Evaluation of the Toxicity, Medicinal Use and Pharmacological Actions of Calotropis Procera", European Journal of Pharmaceutical and Medicinal Research, 2016, vol. 3, No. 9, pp. 28-36.

(Continued)

*Primary Examiner* — Qiuwen Mi

(74) *Attorney, Agent, or Firm* — Vorys, Sater, Seymour and Pease LLP; Anthony P. Venturino

(57) ABSTRACT

Provided are compositions including at least one Dead Sea extract and at least one extract of the Apple of Sodom (*Calotropis procera*). Further provided are formulations including the compositions and their uses.

16 Claims, 16 Drawing Sheets

(56) References Cited

OTHER PUBLICATIONS

Kumar et al., "*Calotropis procera* Root Extract Has the Capability to Combat Free Radical Mediated Damage", ISRN Pharmacology, Hindawi Publishing Corporation, 2013, vol. 2013, Article ID 691372, 8 pages.

Ma'or et al., "Skin smoothing effects of Dead Sea minerals: comparative profilometric evaluation of skin surface", International Journal of Cosmetic Science, 1997, vol. 19, pp. 105-110.

Moronkola et al., "Chemical compositions of leaf and stem essential oils of Calotropis procera Ait R.Br [Asclepiadaceae]", Der Chemica Sinica, 2011, vol. 2, No. 2, pp. 255-260.

Moses et al., "The Dead Sea, A Unique Natural Health Resort", IMAJ, 2006, vol. 8, pp. 483-488.

Parihar et al., "Anti inflammatory effect of *Calotropis procera* root bark extract." Asian Journal of Pharmacy & Life Science, 2011, vol. 1, No. 1, pp. 29-44.

Sheth et al., "Ethnobotanical studies and validation of lead: a case study on evaluation of *Calotropis* sp. on dermal fungal infections", International Journal of Pharmacy & Life Sciences, 2011, vol. 2, Issue 6, 797-800.

Subramanian et al., "Gene set enrichment analysis: A knowledge-based approach for interpreting genome-wide expression profiles", PNAS, 2005, vol. 102, No. 43, pp. 15545-15550.

Sukenik et al., "Treatment of Psoriatic Arthritis at the Dead Sea", The Journal of Rheumatology, 1994, vol. 21, pp. 1305-1309.

Tripathi et al., "Callus culture and in vitro biosynthesis of cardiac glycosides from *Calotropis gigantea* (L.) Ait", In Vitro Cell. Dev. Biol.—Plant, 2013, vol. 49, Issue 4, pp. 455-460.

\* cited by examiner

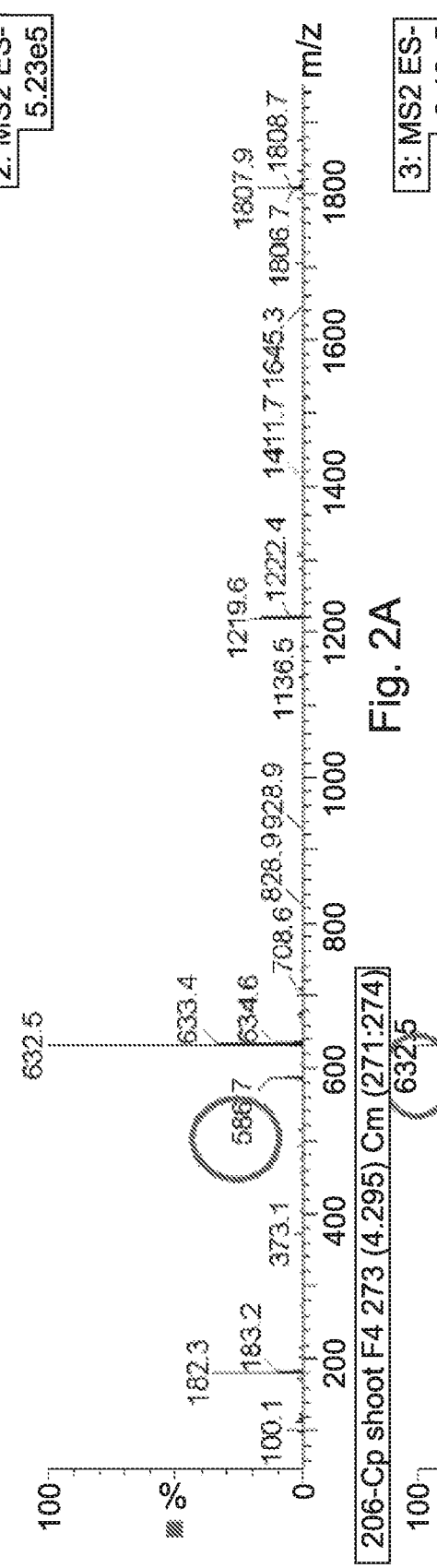
Fig. 2A
Fig. 2B

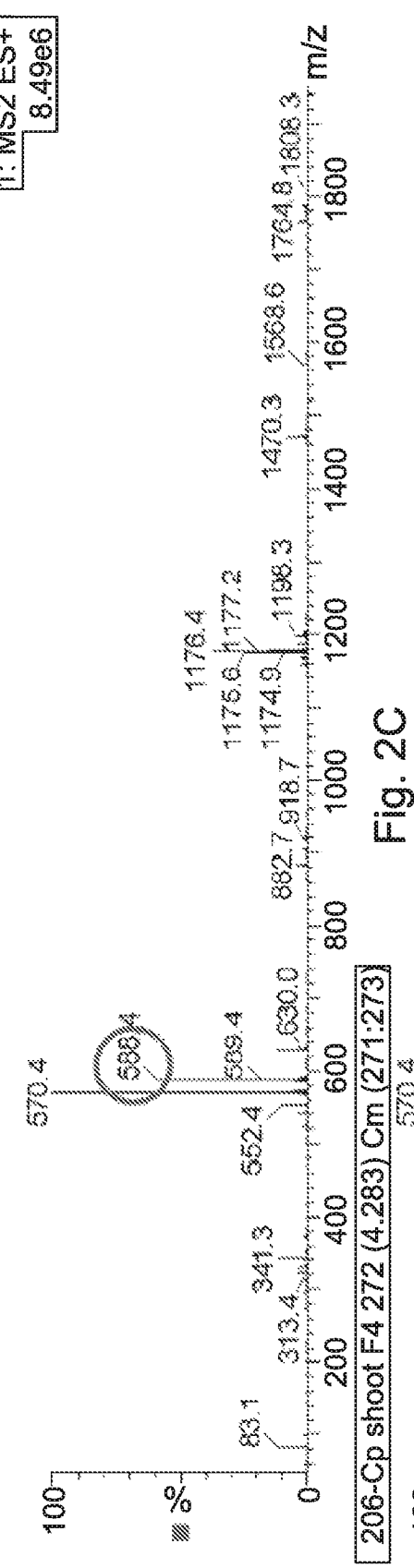
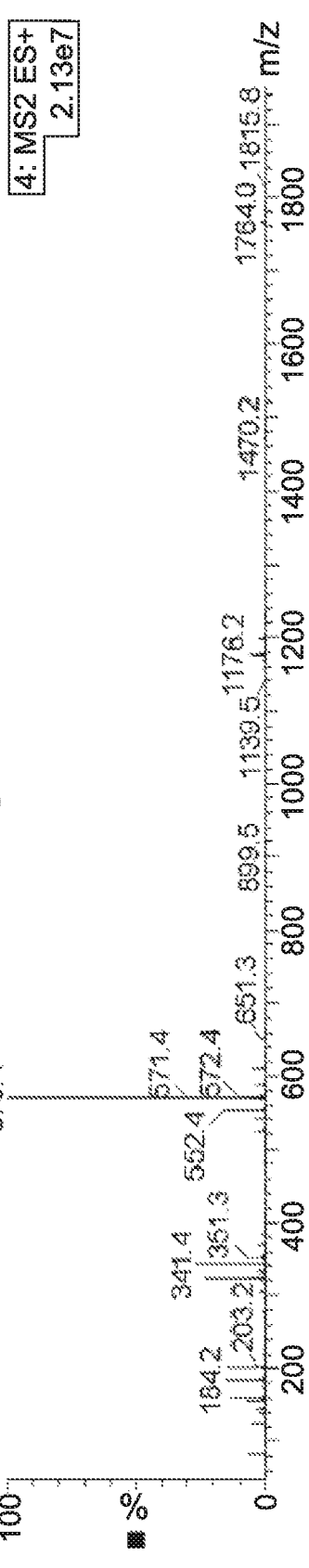
Fig. 2C
Fig. 2D

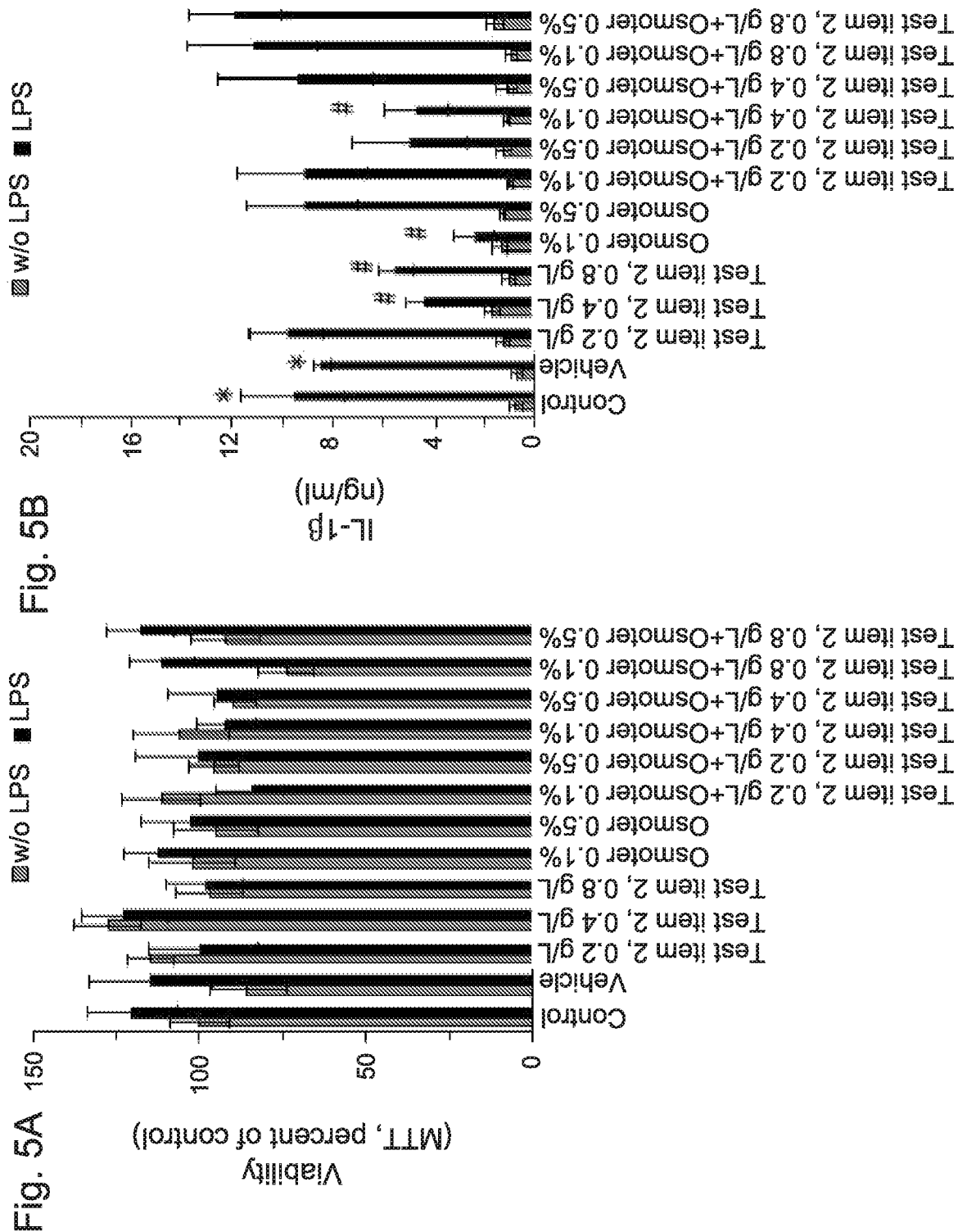

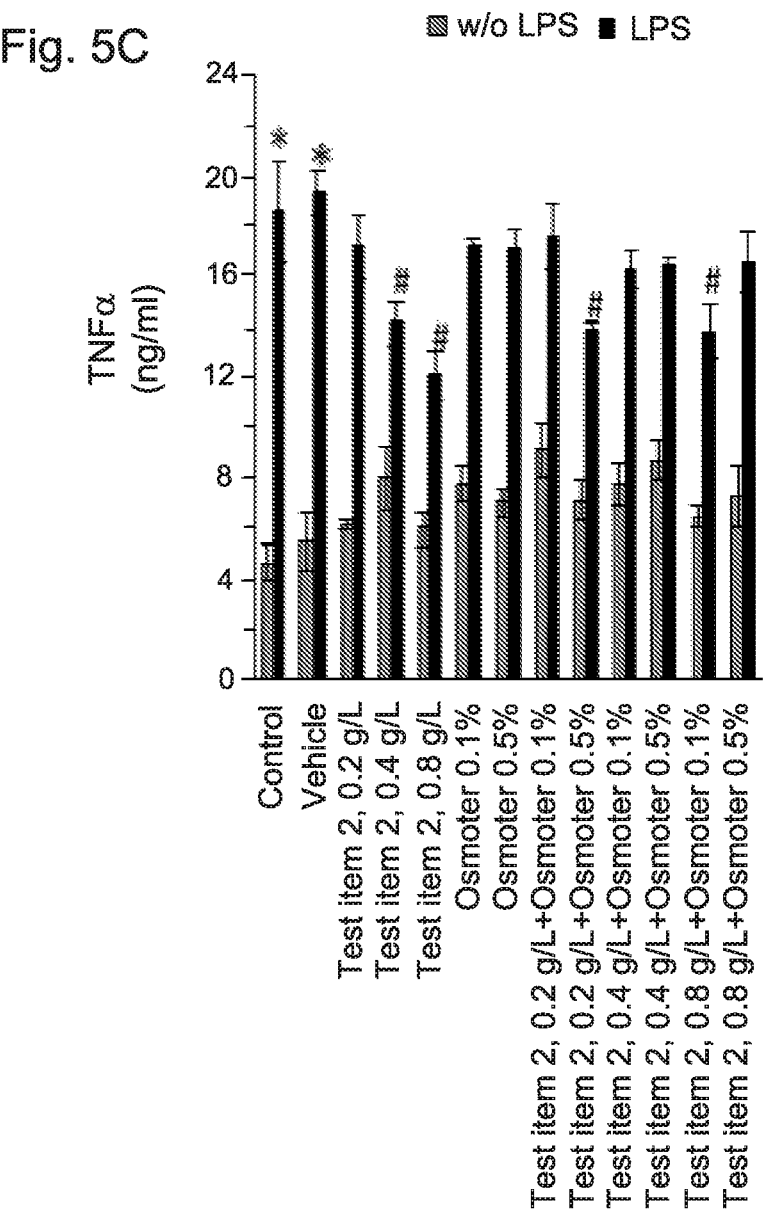

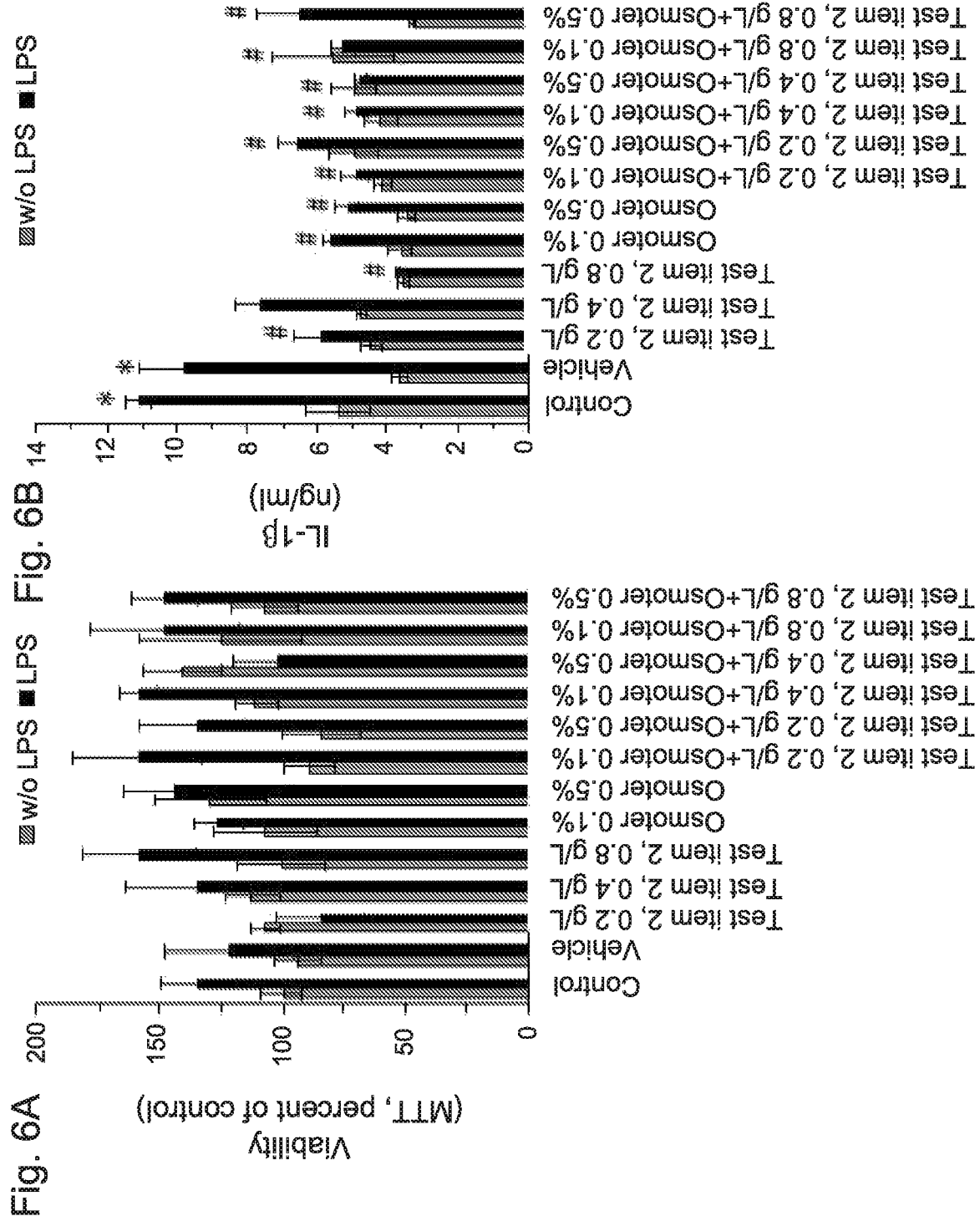

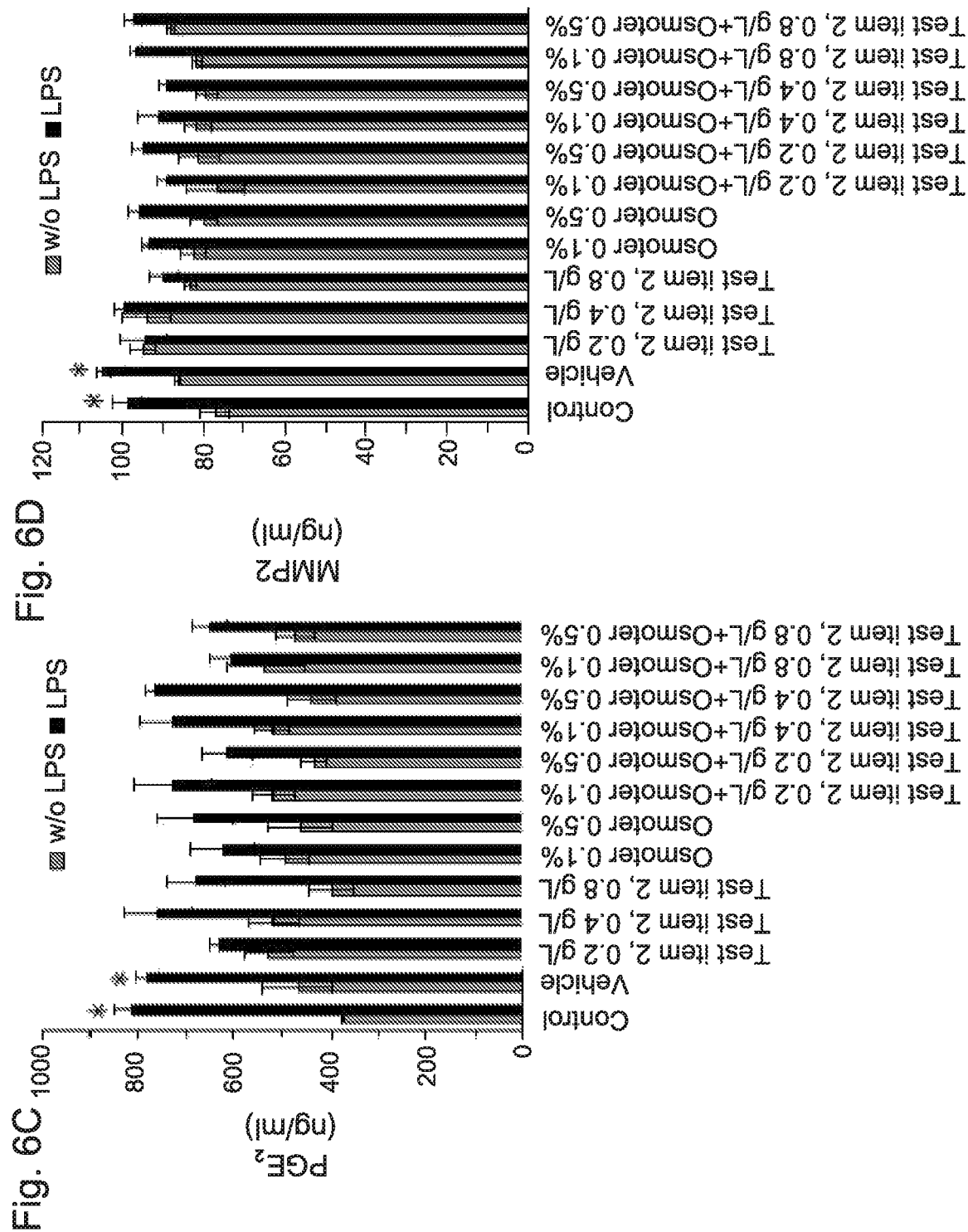

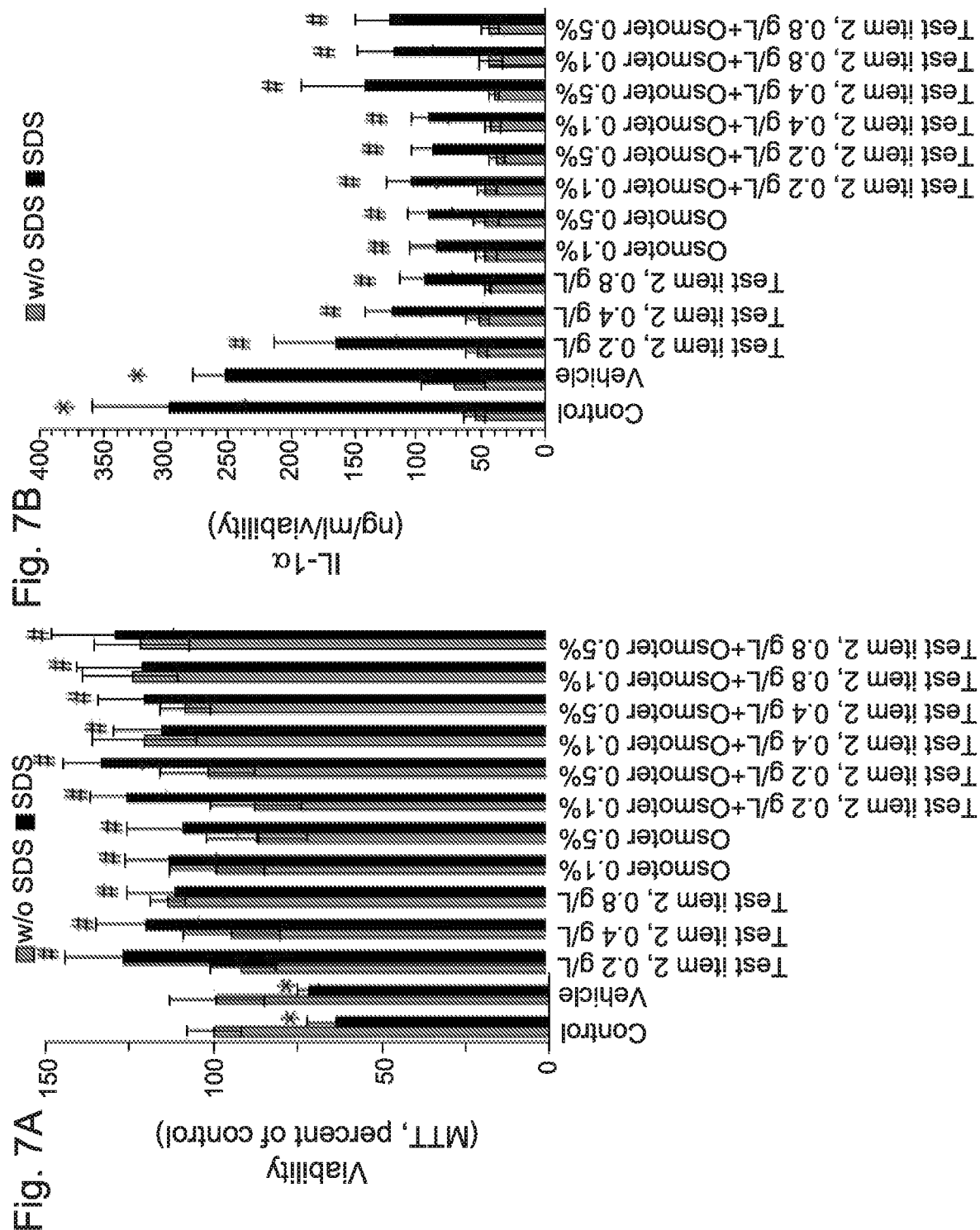

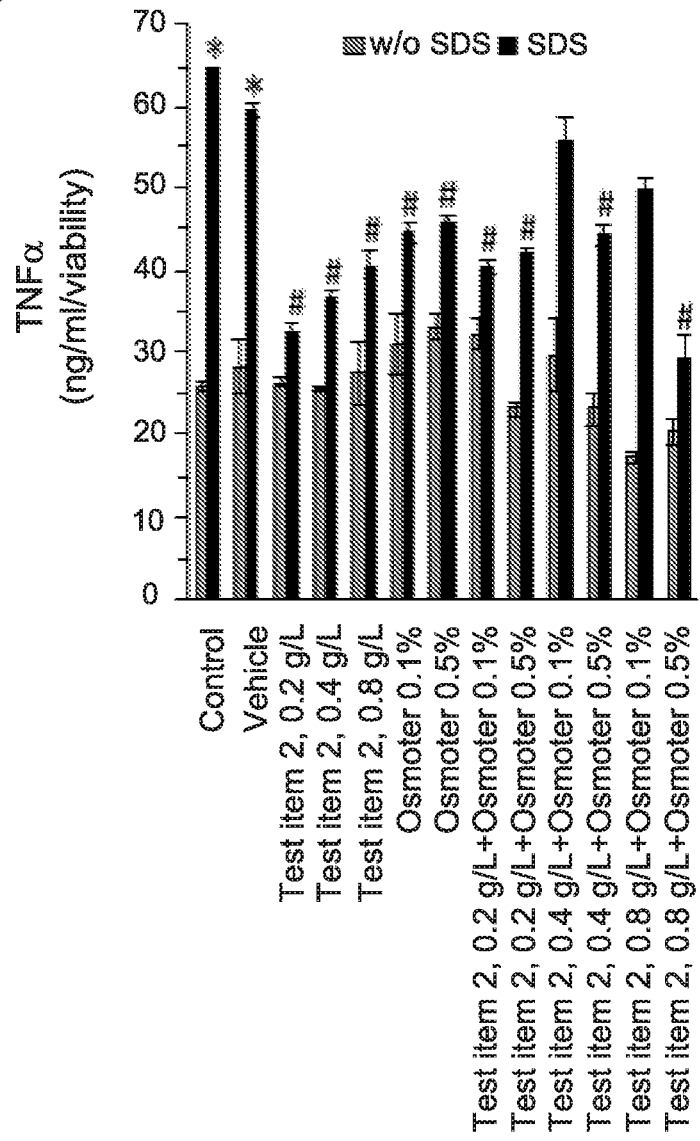

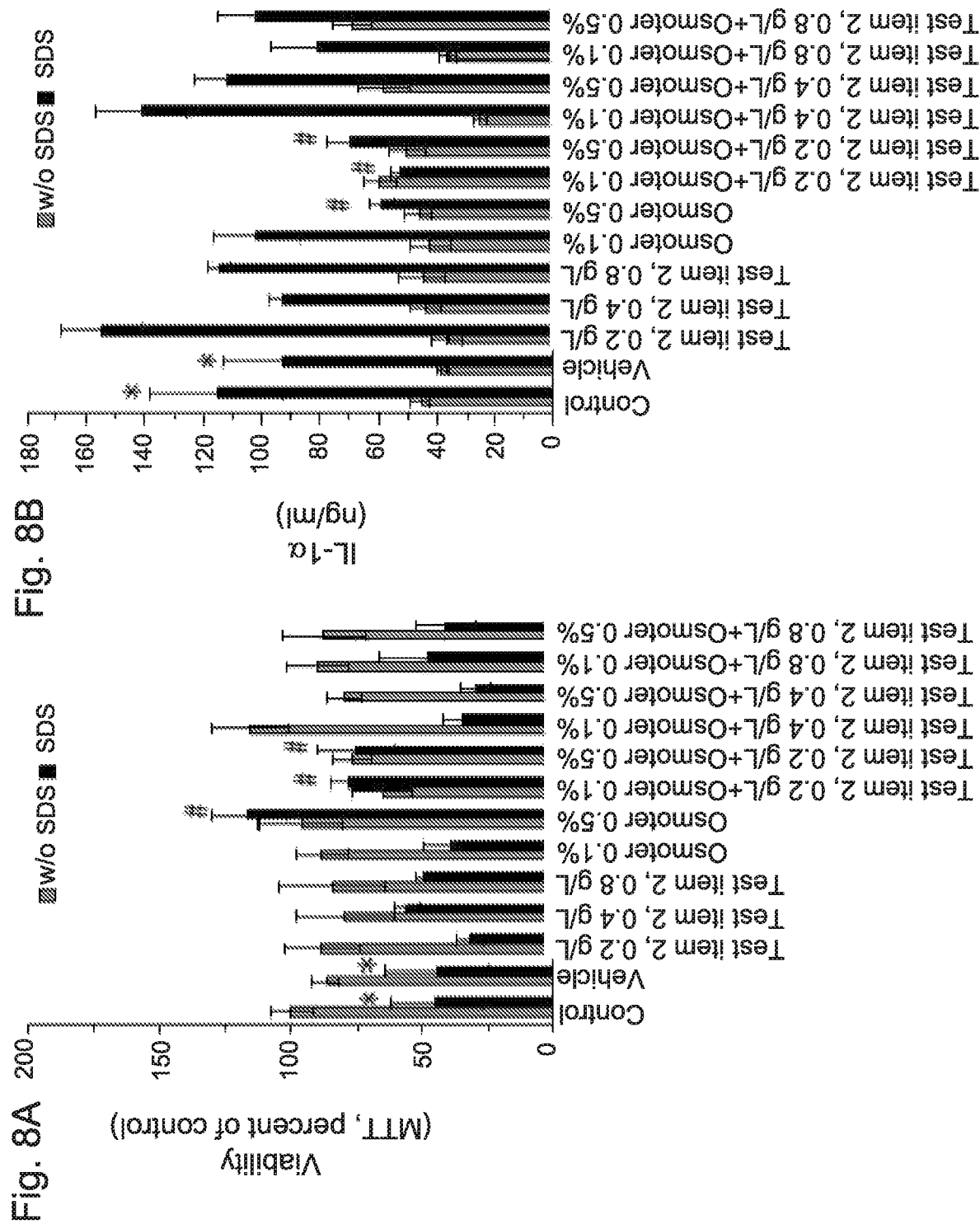

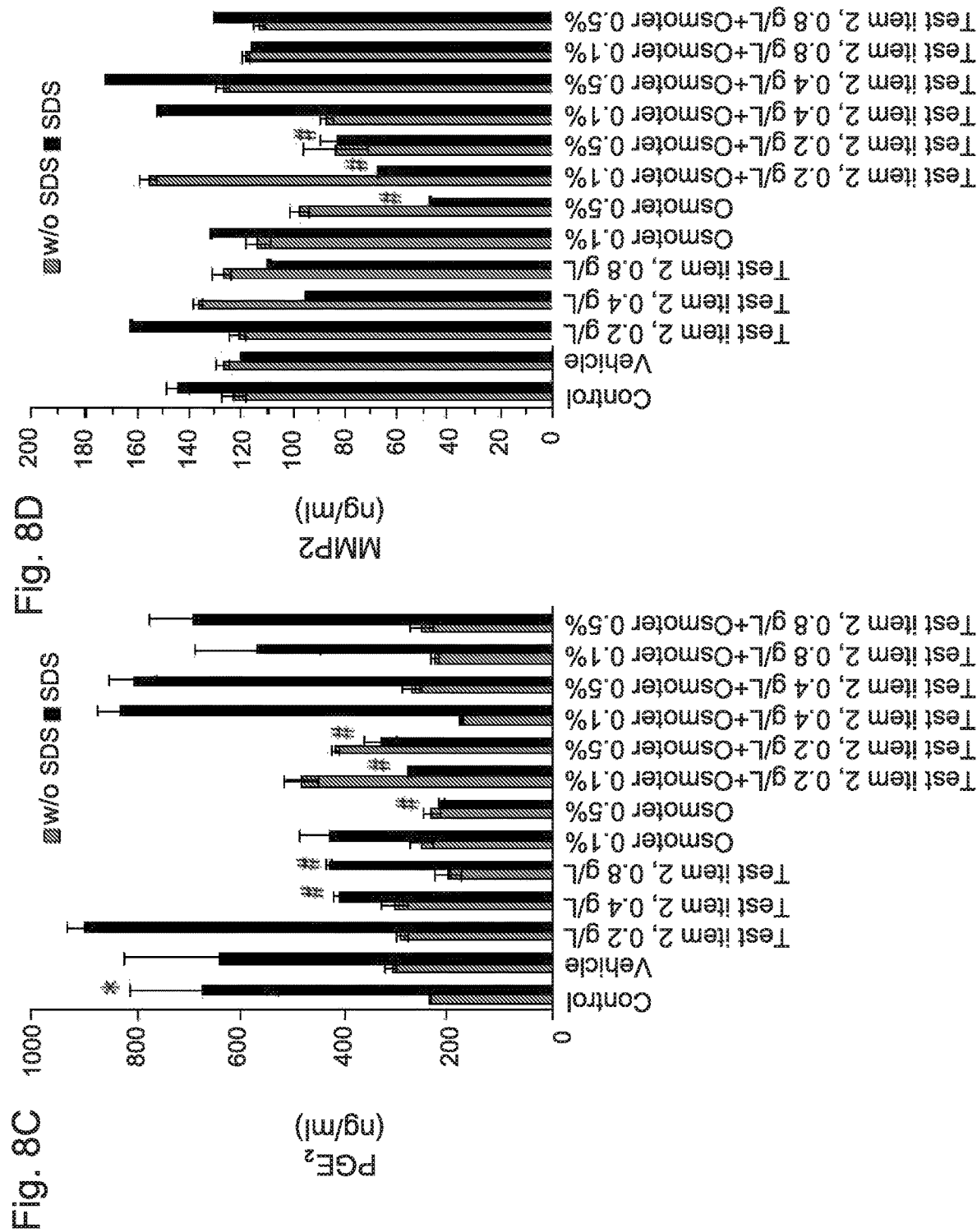

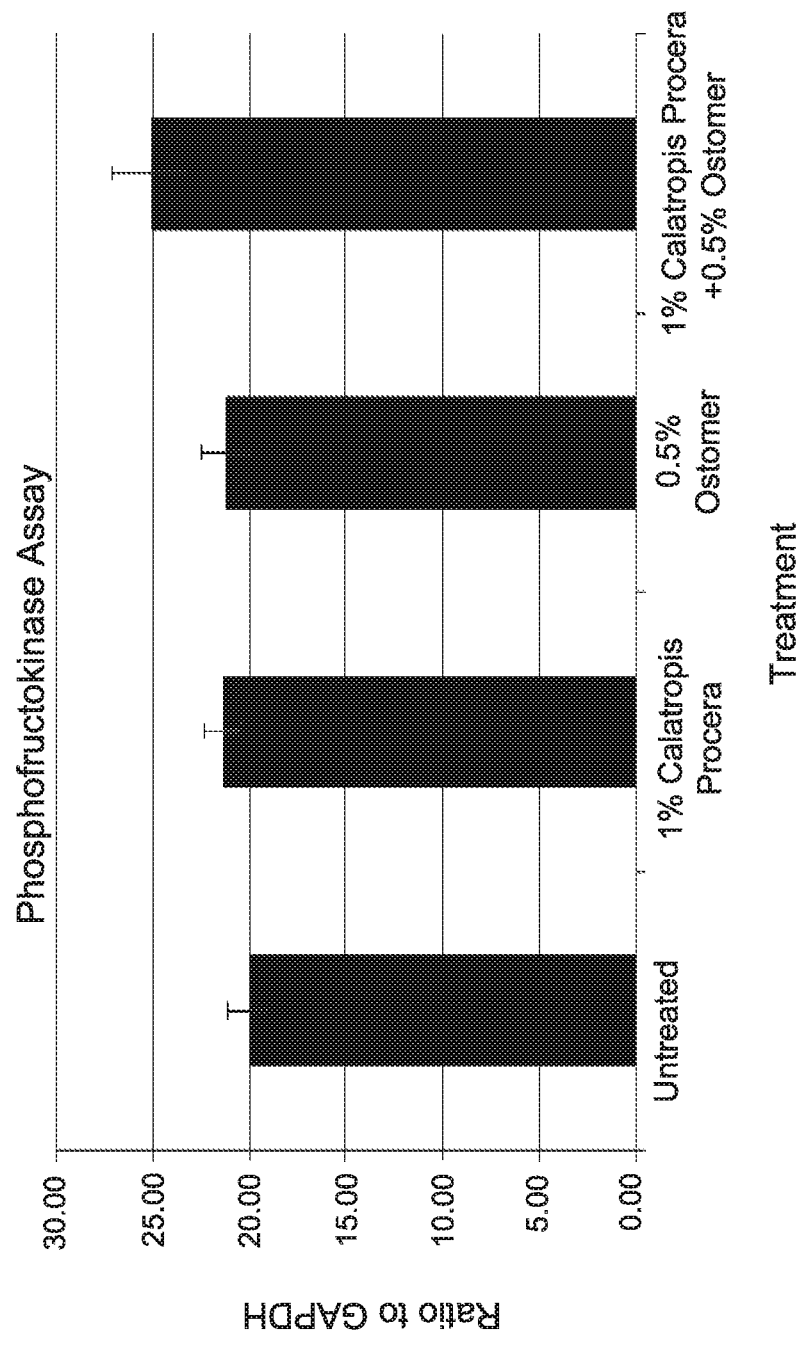

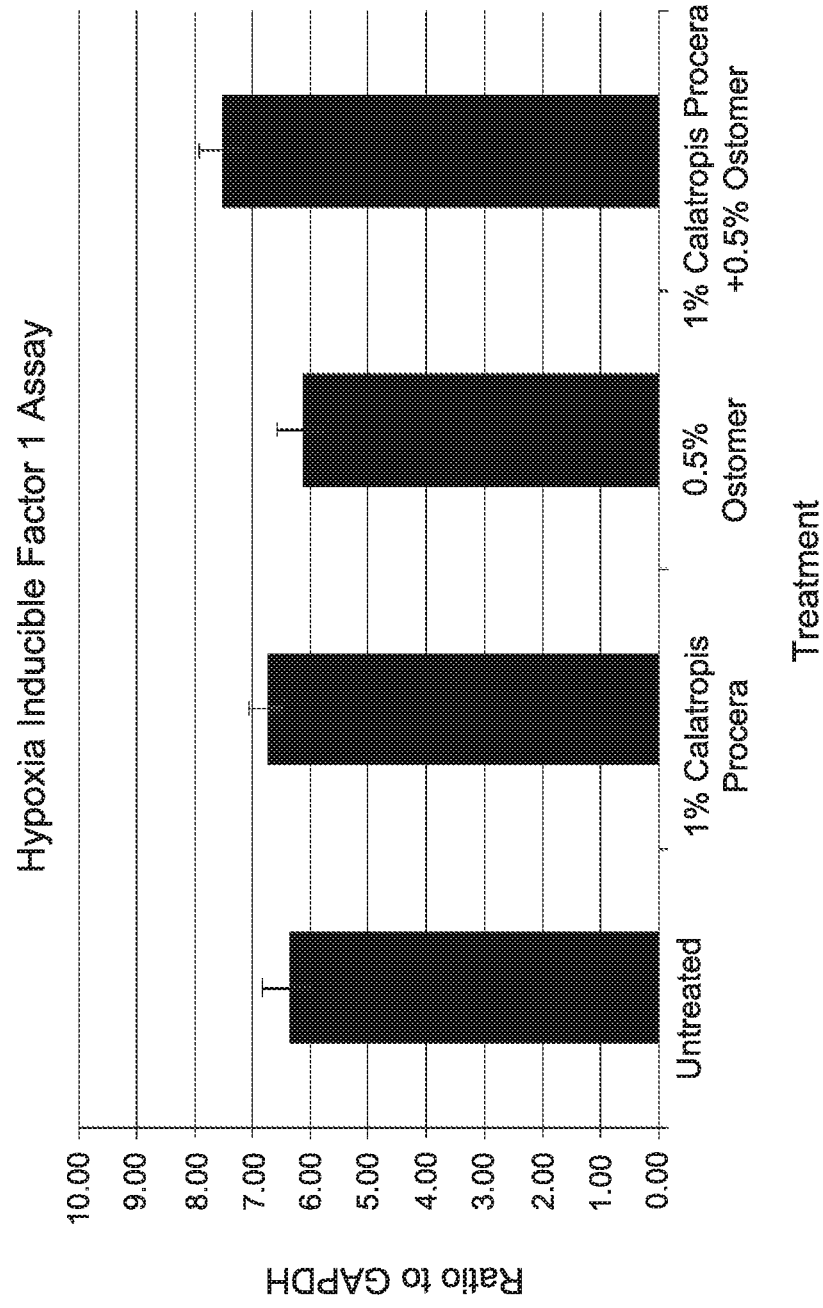

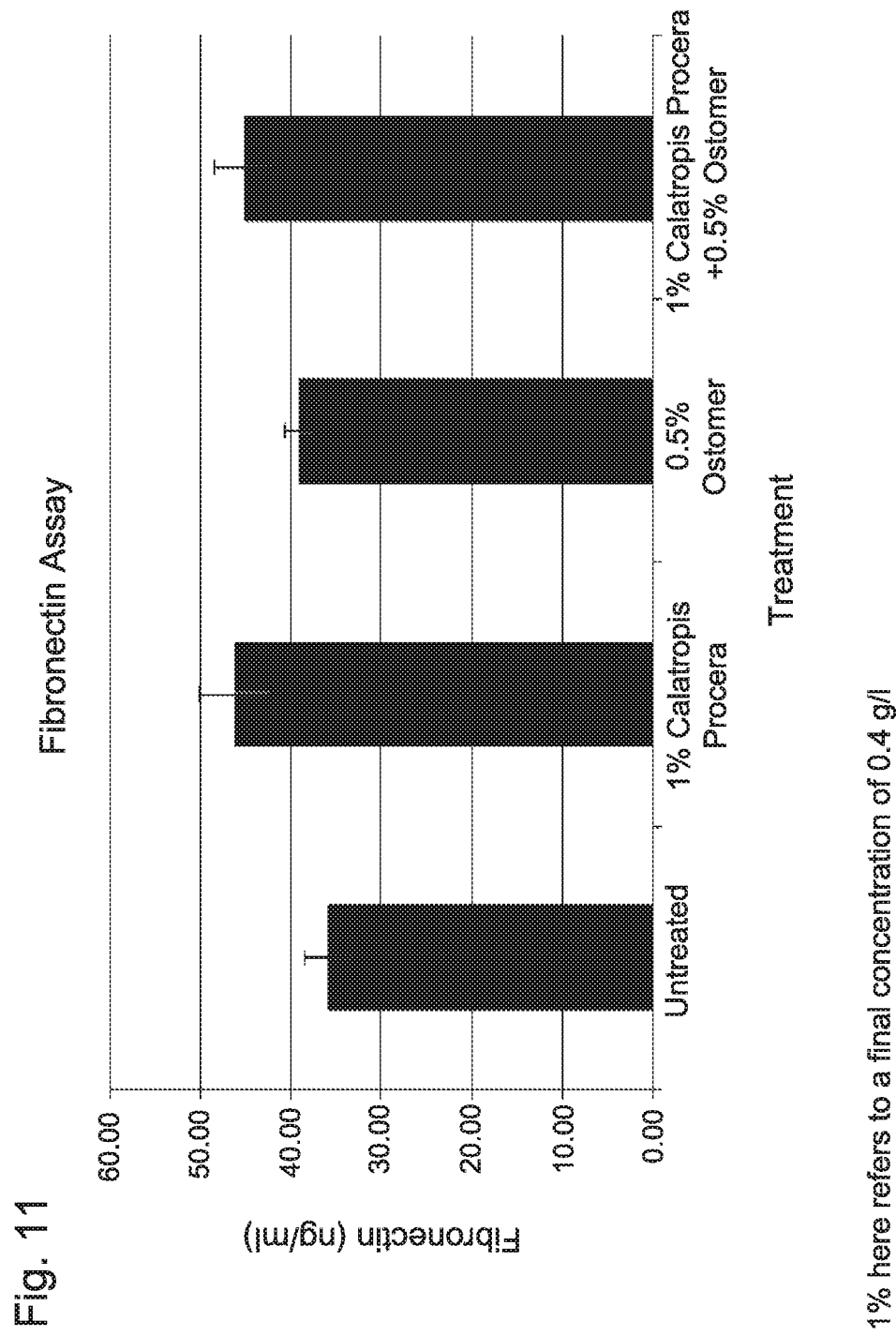

COMPOSITIONS COMPRISING DEAD SEA EXTRACT AND AN EXTRACT OF APPLE OF SODOM AND USES THEREOF

FIELD OF THE INVENTION

This invention relates to compositions comprising Dead Sea extract in combination with an extract of the Apple of Sodom (*Calotropis procera*) and their uses.

BACKGROUND OF THE INVENTION

Therapeutic and to some extent even cosmetic skin formulations are aimed at replenishing skin moisture; protecting against on-going loss of moisture; removing dead skin cells; decreasing irritation; minimizing irritant release; and minimizing skin conditions associated with e.g., inflammation are among the most sought after formulations. The inclusion of extracts of plants and extracts isolated from other natural sources or the replacement of synthetic medicaments traditionally used for such purposes by such natural extracts has been proposed not only for reducing undesired toxicity but also for attracting the end user to such greener formulations.

Apple of Sodom (AoS) (*Calotropis procera*) is a small tree with grey-white trunk and branches, a thick layer of cork covering the trunk, large, green fleshy leaves, large dark purple flowers and apple like fruits but hollow, full with seeds with long hairy fringes. AoS specie belongs to the dogbane family, Apocynaceae (sub family Asclepiadaceae), that is native to the Dead Sea area, North Africa, Tropical Africa, Western Asia, and South Asia especially Indochina. The English name of the plant is related to the legend of Sodom and Gomorrah. It is also known by various names like swallow wort, Dead Sea apple, Sodom apple, Stabragh, Kapok tree, King's crown, Rubber bush, Rubber tree or milk weed. The plant has hollow green globes but the flesh thereof contains a toxic milky sap.

The milky sap of *Calotropis procera* contains a complex mix of chemicals, some of which are steroidal heart poisons. One such compound is the Calotropis glycosides called Calotropin.

Despite its toxic potential, *Calotropis procera* presents also healing powers and has been used in Ayurveda medicine (a system of Hindu traditional medicine known for centuries) [1].

Modern medical research is still underway on the properties of *Calotropis procera*.

*Calotropis procera* is known of its antifungal properties wherein it is used to cure skin fungal diseases such as athlete's foot and ringworm [2].

*Calotropis procera* is also known of its anti-inflammatory properties and anti-carcinogenic properties [3, 4].

Kumar et al. [5] describes an extract of dried latex (DL) of *Calotropis procera* for the treatment and prevention of cancer by oral administration.

Kennedy Lina [6] describes a natural composition for topical application to the skin. The composition alleviate post-menstrual symptoms of cramping, backache, breast tenderness and other aches and pains. The composition includes active natural ingredients of *Carapa procera* and *Calotropis procera* with Shea butter and Soy-oil. The Shea butter and plants work together to relieve many aches and pains.

Darro et al. [7], [8], [9] describe an extract of the plant *Calotropis procera*, having a pharmacological activity, in particular an anti-tumor activity and/or an anti-poisonous activity, and active compounds isolated from the extract.

Streeper et al. [10] describe topical and oral formulations of cardiac glycosides for treating skin diseases. Cardiac glycosides from various plants are describe inter-alia from *Calotropis procera*.

EL-Bakry A. A., [11] describe the production of cardiac glycosides from *Calotropis procera* by cell suspension cultures.

Dead Sea water, salts, minerals and mud are well known for their therapeutic efficacy in treating a variety of skin conditions such as psoriasis, atopic dermatitis, acne and other inflammation skin diseases as well as for their cosmetic benefits [12]-[15].

REFERENCES

[1] Innocent O. Imosemi., *Evaluation of the toxicity, medicinal use and pharmacological actions of Calotropis procera*, ejpmr, 2016, 3(9), 28-36.

[2] Falguni K. Sheth and Minoo H. Parabia., *Ethnobotanical studies and validation of lead: a case study on evaluation of Calotropis sp. on dermal fungal infections*. Int. J. of Pharm. & Life Sci. (IJPLS), 2011, Vol. 2, Issue 6: June: 797-800.

[3] Gaurav Parihar, Ankur Sharma, Santosh Ghule, Praveen Sharma, Pradeep Deshmukh, DN Srivastava., *Ant-inflammatory effect of Calotropis procera root bark extract*. Asian Journal of Pharmacy & Life Science, 2011, Vol. 1 (1), Jan-Mar, 29-43.

[4] Tenzin Choedon, Ganeshan Mathan, Soneera Arya, Vijay L Kumar, and Vijay Kumar, *Anticancer and cytotoxic properties of the latex of Calotropis procera in a transgenic mouse model of hepatocellular carcinoma*. World J Gastroenterol. 2006, Apr 28; 12(16), 2517-2522.

[5] WO 2005/099730.

[6] WO 2009/155497.

[7] CA 2501240.

[8] WO 2004/032947.

[9] WO 2004/032948.

[10] US 2006/0205679.

[11] EL-Bakry A. A., et al, *Production of cardiac glycosides from calotropis procera by cell suspension cultures*. Journal of Applied Sciences Research, 2011, 7(9), 1375-1385.

[12] Sukenik S., et al., *Treatment of psoriatic arthritis at the Dead Sea*. J. Rheumatol. 1994, 21, 1305-1309.

[13] S. Halevy., et al. *Dead Sea bath salt for the treatment of psoriasis vulgaris: a double-blind controlled study*. Journal of the European Academy of Dermatology and Venereology, 1997, 9, 237-242.

[14] Maor Z. and Yehuda S. *Skin smoothing effects of Dead Sea minerals: comparative profilometric evaluation of skin surface*. International Journal of Cosmetic Science, 1997, 19, 105-110.

[15] Shimon W. Moses, Michael David, Ehud Goldhammer, Asher Tal and Shaul Sukenik. *The Dead Sea, A Unique Natural Health Resort*. IMAJ, 2006, 8, 483-488.

[16] J. Azmir et al. *Techniques for extraction of bioactive compounds from plant materials: A review*. Journal of Food Engineering, 2013, 117, 426-436.

[17] Tripathi et al. *Callus culture and in vitro biosynthesis of cardiac glycosides from Calotropis gigantea (L.) Ait*. In Vitro Cellular & Developmental Biology—Plant, 2013, Volume 49, Issue 4, pp 455-46.

[18] Subramanian el al., *Gene set enrichment analysis: a knowledge-based approach for interpreting genome-wide expression profiles.* PNAS 2005. Oct 25;102(43): 15545-50).

[19] http://software.broadinstitute.org/gsea/msigdb/collections.jsp (MsigDB v6.1, May 2017 release).

SUMMARY OF THE INVENTION

The inventors of the present invention have developed an active combination of natural extract originated from one of the most saltiest bodies of water on earth, the Dead Sea, and an extract of the Apple of Sodom that is native to the Dead Sea area.

As the present application will further disclose, combinations which comprise a natural extract from the Dead Sea and an extract of the AoS have shown biological beneficial properties such as anti-inflammation and anti-irritation properties.

Further, the inventors of the present disclosure have surprisingly found that combinations of Dead Sea extract and an extract of the AoS have positive effect on several biological pathways in both the gene and the protein level. In particular, compositions with Dead Sea water and an aqueous extract of the AoS obtained from callus cells of various ex-plants (e.g., root explants) of AoS produced by Evonik Advanced Botanicals affected the regulation of various genes which are involved in some important biological pathways such as glycolysis, hypoxia, epithelial mesenchymal transition, MTORC1 (mammalian target of rapamycin complex 1) signaling and TNFA (Tumor Necrosis Factor Alpha) signaling via the nuclear transcription factor NF-kappa B (NFKB). The combination of the Dead Sea extract and the AoS extract also altered the expression of various proteins which are related to some of these biological pathways, thus indicating a beneficial active effect of the combination of these two extracts.

Advantageously, the inventors of the present invention have used an extract of the AoS that is produced from induced callus of ex-vitro plants without affecting the local flora and its sustainable growth, thus avoiding any harm to the population and the diversity of this protected plant which is under the danger of extinction.

As the present application will further disclose, the combination comprising a Dead Sea extract and an extract from the AoS has proven to have skin care and therapeutic attributes, particularly skin related, both protective/preventive and therapeutic.

Thus, the present invention provides in one of its aspects a composition comprising at least one Dead Sea extract and at least one extract of the Apple of Sodom (AoS) (*Calotropis procera*).

In another one of its aspects the present invention provides a composition comprising at least one Dead Sea extract and at least one extract of the AoS, wherein the Dead Sea extract is Dead Sea water (or a concentrate thereof) or an aqueous solution having substantially the same salt and mineral content of the Dead Sea water (or a concentrate thereof), and wherein the AoS extract is an aqueous extract of callus cells of AoS (e.g., leaves, roots, leaf blades, seeds, stems, fruits, shoot and barks) which is substantially free of the toxin Calotropin.

In another one of its aspects the present invention provides a composition comprising at least one Dead Sea extract and at least one extract of the AoS, wherein said at least one extract of the AoS (e.g., an aqueous extract) is an extract of callus cells from AoS roots (e.g., root explants).

In another one of its aspects the present invention provides skin-care compositions (formulations) and/or pharmaceutical compositions (formulations).

In yet another one of its aspects the present invention provides compositions for use in the preparation of skin-care and/or pharmaceutical formulations.

In a further one of its aspects the present invention provides compositions for one or more of protecting and/or improving the state of the skin, and preventing and/or treating imperfections of the skin of a subject.

Yet, in a further one of its aspects the present invention provides compositions for treating or preventing at least one disease or disorder e.g., of the skin.

In a further one of its aspect the present invention provides the use of a composition according to the invention for the preparation of a pharmaceutical composition for treating or preventing a disease or disorder e.g., of the skin.

In another one of its aspects the present invention provides one or more of a lotion, an ointment, a gel, a mask, a toner, an essence, a shampoo, a moisturizer, a sunscreen, a cream, a stick, a spray, an aerosol, foam, a paste, a mousse, a solid, semi-solid, or a liquid make-up, a foundation, and an eye make-up comprising the composition according to the invention.

Yet, in a further one of its aspects the present invention provides a method for one or more of protecting and/or improving the state of the skin of a subject and preventing and/or treating imperfections of the skin of a subject in need thereof, wherein the method comprises topically administering the composition according to the invention onto the skin of the subject.

In another one of its aspects the present invention provides a method for treating or preventing a disease or disorder of the skin of a subject (at times treating or preventing irritation and/or inflammation associate with the disease or disorder), the method comprises administering to a subject in need thereof a composition according to the invention.

Yet, in another one of its aspects the present invention provides a method for treating or preventing irritation and/or inflammation of the skin of a subject, the method comprises administering (e.g., topically) to a subject in need thereof a composition according to the invention.

In yet another one of its aspects the present invention provides a method for minimizing skin conditions associate with inflammation and/or irritation, the method comprises topically administering to a subject in need thereof a composition according to the invention.

In another one of its aspects the present invention provides a method for reducing inflammation and/or irritation of the skin, the method comprises topically administering to a subject in need thereof a composition according to the invention.

In a further one of its aspects the present invention provides a method for treating and/or preventing one or more disease or disorder (at times treating or preventing irritation and/or inflammation associate with the disease or disorder), the method comprises administration (e.g., topical) the composition according to the invention to a subject in need thereof, wherein the disease or disorder are associated with and/or are mediated by and/or are affected by and/or are related to one or more of biological pathways beings selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof.

The present invention also provides compositions, extracts, uses and methods as herein defined and exemplified.

BRIEF DESCRIPTION OF THE FIGURES

In order to understand the invention and to see how it may be carried out in practice, embodiments will now be described, by way of non-limiting example only, with reference to the accompanying drawings, in which:

FIGS. 2A-2D represent the mass spectra (positive and negative mode, FIGS. 2A-2B and FIGS. 2C-2D, respectively) from hypothetic cardenolide obtained from leaves of Apple of Sodom according to some embodiments of the invention.

FIGS. 5A-5C illustrate the impact of Osmoter™, Apple of Sodom extract and their combinations on skin viability, IL-1a and TNFα cytokine induction by Lipo Poly Saccharide (LPS) induced inflammation according to some embodiments of the invention.

FIGS. 6A-6D illustrate the impact of Osmoter™, Apple of Sodom extract and their combinations on skin viability, IL-1a cytokine induction, Prostaglandin 2 ($PGE_2$) synthesis and matrix metalo-proteinase (MMP) activation by LPS induced inflammation according to some embodiments of the invention.

FIGS. 7A-7C illustrate the impact of Osmoter™, Apple of Sodom extract and their combinations on skin viability, IL-1a and TNFα cytokine induction by sodium dodecyl sulfate (SDS) induced irritation according to some embodiments of the invention.

FIGS. 8A-8D illustrate the impact of Osmoter™, Apple of Sodom extract and their combinations on skin viability, IL-1a cytokine induction, Prostaglandin 2 ($PGE_2$) synthesis and matrix metalo-proteinase (MMP) activation by SDS-induced irritation according to some embodiments of the invention.

FIG. 9. illustrate the Phosphofructokinase assay results observed according to some embodiments of the invention.

FIG. 10. illustrate the Hypoxia Induced Factor 1 assay results observed according to some embodiments of the invention.

FIG. 11. illustrate the Fibronectin assay results observed according to some embodiments of the invention.

DETAILED DESCRIPTION OF THE INVENTION

Figure 1:
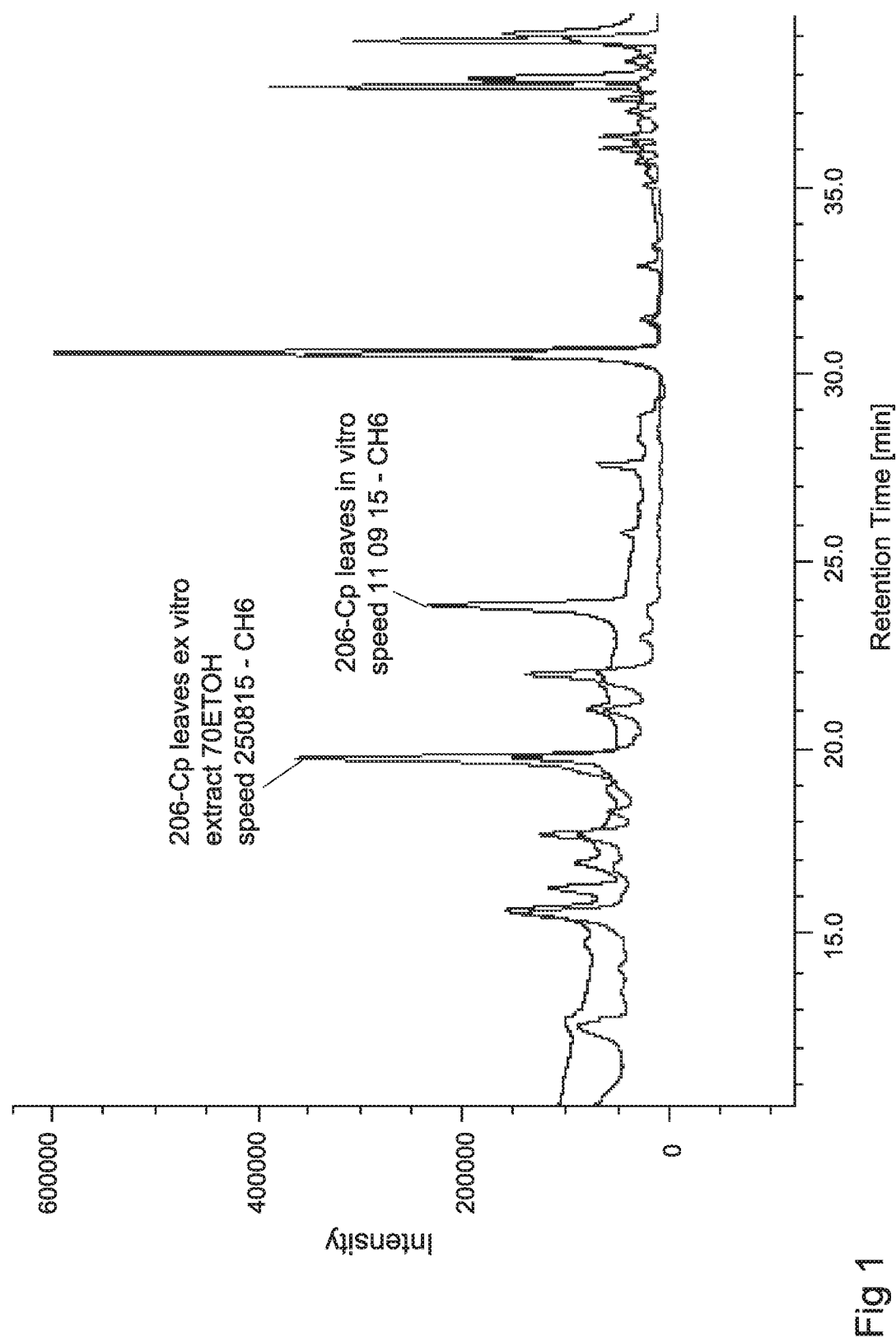
FIG. 1 represents the HPLC profiles of leaf ethanolic extracts from in vitro and ex-vitro cultures according to some embodiments of the invention.

The present invention provides in one of its aspects a composition comprising (as an active combination) at least one Dead Sea extract and at least one extract of the Apple of Sodom (AoS) (*Calotropis procera*).

As used herein, the expression "active combination" refers to the ability of the combination to exert a protective/preventive skin-care/therapeutic effect, as disclosed herein. Neither of the components is regarded as a carrier, diluent or excipient.

As used herein the term "Dead Sea extract" refers to one or more natural material, in the form of a single material (e.g., inorganic, organic, salt, etc.) or a mixture of natural materials obtained from the waters of the Dead Sea and/or the mud surrounding the Dead Sea and/or the soil bed of the Dead Sea.

In some embodiments the Dead Sea extract is a mixture of natural materials (e.g., salts, minerals) obtained from the waters of the Dead Sea and/or the mud surrounding the Dead Sea and/or the soil bed of the Dead Sea.

In some embodiments the Dead Sea extract is a mixture of natural materials (e.g., salts, minerals) obtained from the waters of the Dead Sea.

In some embodiments, the Dead Sea extract is the Dead Sea water.

As used herein the term "Dead Sea water" (herein abbreviated DSW) refers to the saline waters obtained from the Dead Sea (Israel or Jordan) region or an aqueous solution prepared by dissolving Dead Sea minerals in an aqueous medium. The term also encompasses aqueous solutions which simulate such natural solution, namely having at least one parameter substantially identical to that measured for the natural DSW, said parameter being at least one of salt content, at least one of mineral content, salt concentration, concentration of a particular cation or anion, ratio of divalent cations to monovalent cations, TDS (Total Dissolved Salt, w/v), soluble natural substances, and other parameters known to define or characterize natural DSW.

In some embodiments the Dead Sea extract is an aqueous solution having salt and mineral content substantially identical to that measured for the natural DSW.

In some embodiments the Dead Sea extract is an aqueous solution having substantially the same salt (a hypersaline concentration) and mineral content as that of the Dead Sea water.

In some embodiments, the Dead Sea extract is the Dead Sea water which may be obtained directly from the Dead Sea filtered water substantially having the same salt content (a hypersaline concentration) as that of the unfiltered Dead Sea water, or Dead Sea water treated by any one or more of various other methods employed to e.g., remove organic matter and residual contaminants therefrom.

In some embodiments, the Dead Sea extract is an aqueous solution simulating the content of DSW i.e., having substantially identical content as that of DSW.

In some embodiments, the Dead Sea extract is an aqueous solution having substantially identical salts content, minerals content, salts concentration and mineral concentrations as that of DSW.

In some embodiments, the Dead Sea extract is an aqueous solution having substantially identical salts content, minerals content, salts concentration, minerals concentrations, concentration of a particular cation or anion, ratio of divalent cations to monovalent cations, TDS, soluble natural substances and other parameters known to define or characterize natural DSW.

In some embodiments, the Dead Sea extract is an aqueous solution simulating the salt content (a hypersaline concentration) of DSW i.e., having salt content substantially identical to that of DSW.

In some embodiments, the Dead Sea extract is an aqueous solution simulating the (mineral content of DSW i.e., having mineral content substantially identical to that of DSW.

In some embodiments, the Dead Sea extract is an aqueous solution simulating the salt content (a hypersaline concentration) and the mineral content of DSW i.e., having salt content substantially identical to that of DSW and mineral content substantially identical to that of DSW.

In some embodiments, the Dead Sea water having:
1. a specific density of 1.25-1.35 g/ml,
2. pH=4.6-5.6 (at 25° C.), and/or
3. less than 100 cfu/g of non-pathogenic microbes.

The Dead Sea water having the above physical characteristics is a concentrated extract of Dead Sea water comprising (among other metal salt ions) $Ca^{+2}$, $Mg^{+2}$, $Na^+$ and $K^+$ and high concentrations of anions such as $Cl^-$ and $Br^-$.

In some embodiments, the DSW is a clear colorless viscous liquid (at 25° C.).

In some embodiments, the concentrations of these ions are, as assessed by a water analysis carried out by the Geological Survey of Israel:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 1800-3200 mg/L
Potassium ($K^+$): 2,500 mg/L, and
Bromide ($Br^-$): 10,000-12,000 mg/L.
Other minerals may also exist in the waters.

In some embodiments, the Dead Sea Water comprises:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 2400-3200 mg/L
Potassium ($K^+$): 2,500 mg/L, and
Bromide ($Br^-$): 10,000-12,000 mg/L.
Other minerals may also exist in the waters.

In some embodiments, the Dead Sea Water comprises:
Calcium ($Ca^{+2}$): 5,000-10,000 mg/L
Chloride ($Cl^-$): 315,000-360,000 mg/L
Magnesium ($Mg^{+2}$): 100,000-150,000 mg/L
Sodium ($Na^+$): 1800-2200 mg/L
Potassium ($K^+$): 1,000-2,000 mg/L, and
Bromide ($Br^-$): 5,000-10,000 mg/L.
Other minerals may also exist in the waters.

In some further embodiments, the Dead Sea Water comprises:
Calcium ($Ca^{+2}$) 34,000-40,000 mg/L
Chloride ($Cl^-$) 320,000-370,000 mg/L
Magnesium ($Mg^{+2}$) 90,000-95,000 mg/L
Potassium ($K^+$) 1,300-2,200 mg/L
Sodium ($Na^+$) 1,500-2,800 mg/L
Bromide ($Br^-$) 11,000-15,000 mg/L.
Other minerals may also exist in the waters.

In some embodiments, the Dead Sea Water comprises:
Calcium ($Ca^{+2}$): 38,000 mg/L
Chloride ($Cl^-$): 345,000 mg/L
Magnesium ($Mg^{+2}$): 92,500 mg/L
Sodium ($Na^+$): 2000 mg/L
Strontium ($Sr^{+2}$): 800 mg/L
Potassium ($K^+$): 1,400 mg/L, and
Bromide ($Br^-$): 11,500 mg/L.
Other minerals may also exist in the waters.

In some embodiments, the Dead Sea Water comprises:
Calcium ($Ca^{+2}$): 38,000 mg/L
Chloride ($Cl^-$) 345,000 mg/L
Magnesium ($Mg^{+2}$): 92,500 mg/L
Sodium ($Na^+$): 2000 mg/L
Strontium ($Sr^{+2}$): 800 mg/L
Potassium ($K^+$): 1,400 mg/L, and
Bromide ($Br^-$): 11,500 mg/L.
Other minerals may also exist in the waters.

In some embodiments, the DSW is natural DSW which has undergone pre-treatment, e.g., having been concentrated by allowing water to evaporate, for example through solar evaporation, thereafter reconstituted to afford a solution.

In some embodiments the Dead Sea extract is Dead Sea Water preparation commercially available as "Maris Sal" or "Maris Aqua" (AHAVA, Israel) referred to herein below also as "Osmoter".

In some embodiments the Dead Sea extract is Dead Sea mud.

The Dead Sea extract is typically an active fraction having by itself at least one attribute which may be enhanced in a combination with the AoS extract.

In some embodiments the concentration of the Dead Sea extract (e.g., Dead Sea water) in the composition (or formulation) of the invention is at least about 0.01% (w/w). At time is it about 0.1%, 0.2%, 0.3%, 0.4%, 0.5%, 0.6%, 0.7%. 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4% and 2.5%. Any value which is between any one of the above values is within the scope of the present disclosure, e.g., between about 0.01, 0.02, 0.03, 0.04, 0.05 . . . 1.01, 1.02, 1.03, 1.04, 1.05 etc. to . . . 2.41, 2.42, 2.43, 2.44., 2.45, 2.46, 2.47, 2.48, 2.49, 2.50.

In some embodiments the concentration of the Dead Sea extract (e.g., Dead Sea water) in the composition (or formulation) of the invention is at least about 0.01 (g/L). At time is it about 0.01, 0.02, 0.03, 0.04, 0.05, 0.06, 0.07, 0.08, 0.09, 0.1, 0.2, 0.3, 0.4, 0.5, 0.6, 0.7. 0.8, 0.9, 1.0, 2.0, 3.0, 4.0, 5.0 g/L. Any value between the above noted values is within the scope of the present disclosure e.g., 0.01, 0.02, 0.03, . . . 0.11, 0.12, 0.13, 0.14, 0.15, 0.16, 0.17, 0.18, 0.19, 0.20, 0.21, 0.22, 0.23, . . . 0.31, 0.32, 0.33, . . . 0.41, 0.42, 0.43, . . . 0.91, 0.92, 0.93 . . . 1.01, 1.02, 1.03 . . . 2.01, 2.02, 2.03 . . . ,3.01, 3.02, 3.03, . . . 4.01, 4.02, 4.03 . . . etc.

In some embodiments the concentration of the Dead Sea extract (e.g., Dead Sea water) in the composition (or formulation) of the invention is 1.0 g/L.

In some embodiments the concentration of the Dead Sea extract (e.g., Dead Sea water) in the composition (or formulation) of the invention is 2.0 g/L.

In some embodiments the concentration of the Dead Sea extract (e.g., Dead Sea water) in the composition (or formulation) of the invention is 3.0 g/L.

In some embodiments the concentration of the Dead Sea extract (e.g., Dead Sea water) in the composition (or formulation) of the invention is 4.0 g/L.

In some embodiments the concentration of the Dead Sea extract (e.g., Dead Sea water) in the composition (or formulation) of the invention is 5.0 g/L.

The AoS extract is typically an active fraction having by itself at least one attribute which may be enhanced in a combination with the Dead Sea extract.

The AoS extract may be obtained according to known procedures. For example, J. Azmir et. al., [16] (the content thereof is incorporated herein by reference) provide a review of conventional as well as non-conventional extraction techniques. EL-Bakry A. A., [11] (the content thereof is incorporated herein by reference) describe a procedure of culturing of *Calotropis procera* callus cells in suspension. A process of extracting the plant cell mass is also described therein. Various extracts of AoS are also commercially available.

The term "AoS extract" or any lingual variations thereof relates to a fraction obtained from the whole plant or one or more parts (organs) thereof e.g., roots, leaves, leaf blades, seeds, stems, fruits, shoot and barks (peel). At times, the term also encompassed an extract of culture cells obtained from callus induction from one or more parts of the plant. At times the cells are undifferentiated cells.

In some embodiments the AoS extract is a whole plant extract, including flesh and latex.

In some embodiments the AoS extract is an ex-plant extract.

In some embodiments the AoS extract is an ex-vitro plant extract.

In some embodiments the AoS extract is an ex-vitro explant extract.

In some embodiments the AoS extract is an extract of one or more of roots, leaves, leaf blades, seeds, stems, fruits and barks (peel).

In some embodiments the AoS extract is and extract obtained from the AoS roots.

In some embodiments the AoS extract is and extract obtained from the AoS roots (including flesh and barks).

In some embodiments the AoS extract is and extract obtained from the AoS leaves.

In some embodiments the AoS extract is and extract obtained from the AoS leaf blades.

In some embodiments the AoS extract is and extract obtained from the AoS seeds.

In some embodiments the AoS extract is and extract obtained from the AoS stems.

In some embodiments the AoS extract is and extract obtained from the AoS fruits.

In some embodiments the AoS extract is and extract obtained from the AoS barks (peel).

In some embodiments the AoS extract is a whole plant extract, including flesh and latex.

In some embodiments the AoS extract is AoS callus extract.

In some embodiments the AoS extract is an extract of in vitro plantlets callus.

In some embodiments the AoS extract is an extract of in vitro plants callus.

In some embodiments the AoS extract is an extract of AoS in vitro plantlets leaves.

In some embodiments the AoS extract is an extract of callus cell cultures of AoS in vitro plantlets leaves.

In some embodiments the AoS extract is an extract of AoS in vitro plantlets leaf blades.

In some embodiments the AoS extract is an extract of callus cell cultures of AoS in vitro plantlets leaf blades.

In some embodiments the AoS extract is an extract of AoS in vitro plantlets stems.

In some embodiments the AoS extract is an extract of callus cell cultures of AoS in vitro plantlets stems.

In some embodiments the AoS extract is an extract of AoS in vitro plantlets fruit.

In some embodiments the AoS extract is an extract of callus cell cultures of AoS in vitro plantlets fruits.

In some embodiments the AoS extract is an extract of AoS in vitro plantlets roots.

In some embodiments the AoS extract is an extract of callus cell cultures of AoS in vitro plantlets roots.

In some embodiments the AoS extract is AoS callus extract of one or more of roots, leaves, leaf blades, seeds, stems, fruits, shoot and barks (peel).

In some embodiments the AoS extract is AoS stem cells extract.

In some embodiments the AoS extract is an extract of undifferentiated cells.

In some embodiments the AoS extract is an extract of *Calotropis procera* cell culture/s.

In some embodiments the AoS extract is obtained in a method which comprises culturing *Calotropis procera* callus cells in suspension according to [11] and extracting the plant cell mass.

In some embodiments the AoS extract is obtained by Soxhlet extraction.

In some embodiments the AoS extract is obtained in a process which utilizes dehydration of the plant.

In some embodiments the AoS extract is obtained in a process which does not utilize dehydration of the plant.

In some embodiments the AoS extract is a non-toxic extract produced from a toxic plant (e.g., missing at least one toxic compound which is present in the plant itself).

In some embodiments the AoS extract is a non-toxic extract.

In some embodiments the AoS extract is a callus extract with a lower toxicity compared to the AoS plant itself.

In some embodiments the AoS extract is substantially free of the Calotropin toxin (e.g., as evident from a mass spectrum of the extract which is characterized by absence of a mass peak which is indicative of the Calotropin toxin, see below).

In some embodiments the AoS extract has Mass Spectrum/s as herein described and exemplified.

In some embodiments the AoS extract has an characteristic Mass Spectrum peak at 520 MW e.g., characteristic of the compound Asclepioside.

In some embodiments the AoS extract has HPLC profile/s as herein described and exemplified.

In some embodiments the extract of the AoS plant may be originated from AoS from one or more of Dead Sea area, North Africa area, Tropical Africa area, Western Asia area, South Asia area and Indochina.

In some embodiments the AoS plant from which the extract is obtained may be native to the aforementioned areas or otherwise grown outside of the region, naturally, e.g., due to natural invasion, or for commercial purposes, horticulture purposes or for any other reason.

In some embodiments the extract of the AoS plant is originated from AoS form the Dead Sea area and produced and/or processed as herein described.

In some embodiments the AoS plant from which the extract is obtained may be native to the Dead Sea area or otherwise grown outside of this region, naturally, e.g., due to natural invasion, or for commercial purposes, horticulture purposes or for any other reason.

In some embodiments the AoS from which the extract is obtained may also be one that produced in vitro.

In some embodiments the AoS extract is an extract of in vitro plant.

In some embodiments the AoS extract is an extract of in vitro plantlets.

In some embodiments the AoS extract is an extract of ex vitro plant.

In some embodiments the AoS extract is an extract of ex vitro plantlets.

In some embodiments the AoS extract is an aqueous extract.

In some embodiments the AoS extract is an extract obtained by extraction in 100% water.

In some embodiments the AoS extract is an aqueous extract substantially free of an organic solvent. Non limiting example of such solvent are one or more of petroleum ether, methanol and chloroform.

In some embodiments the AoS extract is an oil extract.

In some embodiments the AoS extract is not an oil extract.

In some embodiments the AoS extract is provided in an oil form.

In some embodiments the AoS extract is not provided in an oil form.

In some embodiments the AoS extract is an alcoholic extract. Non limiting examples of alcohols are ethanol and methanol.

In some embodiments the AoS extract is extract in ethanol.

In some embodiments the AoS extract is an alcoholic extract obtained by extraction in about 70% ethanol and about 30% water.

In some embodiments the AoS extract is a non-alcoholic extract.

In some embodiments the AoS extract is a non-alcoholic aqueous extract.

In some embodiments the AoS extract is obtained from a polar solvent.

In some embodiments the AoS extract is obtained from a non-polar solvent.

In some embodiments the AoS extract is obtained in a method which does not utilize organic solvents (e.g., polar and/or non-polar).

The AoS extract may be a pure (neat) extract or an extract formulated along with a predetermined amount of at least one additive such as a stabilizer, diluent, carrier, filler, antioxidant or any other inert additive.

Is some embodiments the additive is glycerol (e.g., about 80% glycerol).

In some embodiments the concentration of the AoS extract in the composition (or formulation) of the invention is at least about 0.01 (g/L). At time is it about 0.01, 0.02, 0.03, 0.04, 0.05, 0.06, 0.07, 0.08, 0.09,0.1, 0.2, 0.3, 0.4, 0.5, 0.6, 0.7. 0.8, 0.9 and 1.0 g/L. Any value between the above noted values is within the scope of the present disclosure e.g., 0.01, 0.02, 0.03, . . . 0.11, 0.12, 0.13, 0.14, 0.15, 0.16, 0.17, 0.18, 0.19, 0.20, 0.21,0.22, 0.23, . . . 0.31, 0.32, 0.33, . . . 0.41, 0.42, 0.43, . . . 0.91, 0.92, 0.93 etc.

In some embodiments the concentration of the AoS extract in the composition (or formulation) of the invention is 0.1 g/L, at times 0.2 g/L, at times 0.3 g/L, at times 0.4 g/L, at times 0.5 g/L, at times 0.6 g/L, at times 0.7 g/L, at times 0.8 g/L, at times 0.9 g/L, at times 1.0 g/L.

In some embodiments the concentration of the AoS extract in the composition (or formulation) of the invention is 0.2 g/L.

In some embodiments the concentration of the AoS extract in the composition (or formulation) of the invention is 0.4 g/L.

In some embodiments the concentration of the AoS extract in the composition (or formulation) of the invention is 0.8 g/L In some embodiments the AoS extract is an extract as herein described and exemplified.

In some embodiments the compositions of the present invention does not comprise an extract of Carapa procera.

In some embodiments, the composition of the invention is a cosmetic composition. In other embodiments, the composition is a pharmaceutical composition. In further embodiments, the pharmaceutical composition is for topical application.

In some embodiments, the composition is a synergistic composition.

The compositions of the present invention may be made into a wide variety of product forms suitable for, e.g., topical administration onto the skin of a subject. Non-limiting examples are a lotion, an ointment, a gel, a mask, a toner, an essence, a shampoo, a moisturizer, a sunscreen, a cream, a stick, a spray, an aerosol, foam, a paste, a mousse and a variety of cosmetics or skin-care formulations including solid, semi-solid, or a liquid make-up such as foundations, eye make-up, etc.

In some embodiments the liquid may be applied onto the skin as a moisturizer.

In some embodiments, the composition of the invention is formulated as a lotion.

In some embodiments, the composition of the invention is formulated as an emulsion.

In some embodiments, the composition of the invention is formulated as a facial formulation.

In some embodiments, the composition of the invention is formulated as a body formulation.

In some embodiments, the composition of the invention is formulated as a leave on formulation.

In some embodiments, the composition of the invention is formulated as rinse off formulation.

As used herein, a "leave on" (in contrary to "rinse off") composition/formulation refers to a composition/formulation that may be in prolonged contact with the skin and can be applied to a skin region without the need to remove it from the skin (e.g., by wiping or rinsing it off) in any way.

In some embodiments, the leave-on composition/formulation may be adapted to be applied to a skin region and to be left on the skin for a time sufficient to achieve an end result.

The viscosity of the composition according to the invention may vary depending on the form (i.e., lotion, cream, etc.), concentration of the active combination, the carrier, the purpose (i.e., cosmetic or therapeutic), end user and other parameters.

The compositions according to the invention (cosmetic or therapeutic) may comprise at least one dermatological, cosmetically or pharmaceutically acceptable additive selected amongst inert and effect-inducing additives. In some embodiments, the inert additive is selected from a diluent, a preservative, an abrasive, an anti-caking agent, an antistatic agent, a binder, a buffer, a dispersant, an emollient, an emulsifier, a co-emulsifiers, a fibrous material, a film forming agent, a fixative, a foaming agent, a foam stabilizer, a foam booster, a gallant, a lubricant, a moisture barrier agent, an opacifier (e.g., styrene/acrylamide copolymer), a plasticizer, a preservative, a propellant, a stabilizer, a surfactant, a suspending agent, a thickener, a wetting agent, and a liquefier.

In some embodiments, the at least one inert additive is a smoothness enhancer ingredient, such as silica.

In some embodiments, each of the at least one dermatological, cosmetically or pharmaceutically acceptable additives may constitute between about 0.05 to 15% of the total weight of the formulation. In some embodiments, the at least one additive constitutes between 0.05% and 10% or between 0.05% and 8%, or between 0.05% and 7%, or between 0.05% and 6%, or between 0.05% and 5% of the total weight of the formulation.

In some embodiments, the at least one inert additive is a diluent being selected from water, Bisabolol, propane diol, propylene glycol, butylene glycol, glycerin, safflower oil and mixtures thereof.

In some embodiments, the at least one inert additive is a preservative being selected from one or more of methylparaben, methyldibromo glutaronitrile, phenethyl alcohol, glyceryl caprilate, propylparaben, methylisothiazolinone, decylene glycol, dehydroacetic acid, phenoxyethanol, benzoic acid, 2-methyl-2H-isothiazoline-3-one, polyethylene glycol monococoate, polyethylene glycol dicocoate, polyethylene Glycol, iodopropynyl butylcarbamate, 1.2-hexanediol, caprylyl glycol, imidazolidinyl urea, DMDM Hydantoin, Ipbc, MIT, 2,3-bronopol.

In further embodiments, the inert additive is an emulsifier being selected from one or more of cetyl hydroxyethylcellulose, cetyl alcohol, ceteth-20 (a polyethylene glycol derivative of cetyl alcohol), cetearyl olivate, cetyl palmitate, sorbitan olivate, sorbitan palmitate, stearates, steareth-20 (polyethylene glycol ethers of stearic acid- octadecyl polyoxyethylene ether), steareth-25.

In some embodiments, the stearate is selected from PEG-40 stearate, glyceryl steatrate, sorbitan tristearate, stearyl alcohol and mixtures thereof.

In some embodiments, the stearate is glyceryl stearate.

In still other embodiments, the inert additive is an emollient, being selected from vegetable and animal fats and oils such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (matricaria) flower oil, hypericum perforatum oil, soybean oil and vitis vinifera (grape) seed oil; acetoglyceride esters, such as acetylated monoglycerides; alkyl esters of fatty acids having 10 to 24 carbon atoms which include, but are not limited to, methyl, isopropyl, and butyl esters of fatty acids such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, bydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono-and di-fatty acid esters, polyethylene glycol (200-6000) mono-and di-fatty acid esters, propylene glycol mono-and di-fatty acid esters, polypropylene glycol 2000 monooleate, polypropylene glycol 2000 monostearate, glyceryl mono-and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; vegetable waxes including, but not limited to, carnauba and candelilla waxes; surface active silicone derivatives such as cyclopentasiloxane PEG/PPG-18/18 dimethicone, dimethicone, dimethicone crosspolymer, cyclomethicone, cyclomethicone&dimethiconol; caprylic/capric triglyceride; and cholesterol fatty acid esters and any mixtures thereof.

In some embodiments, each of the at least one inert additive may constitute between about 0.05 to 15% of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

In other embodiments, the effect-inducing additive is selected from an anti-acne agent, an anti-aging agent, an antibacterial agent, an anti-cellulites agent, an antidandruff agent, an antifungal agent, an anti-inflammatory agent, an anti-irritation agent (e.g., allantoin, Aloe Barbadensis leaf juice), an antimicrobial agent, an antioxidant (e.g., butylated hydroxyanisole, propyl gallate, an antiperspirant agent, an antiseptic agent, a cell stimulant, a cleansing agent, a conditioner, a deodorant, a fragrance ingredient (e.g., perfume, limonene), a depilatory, a detergent, an enzyme, an essential oil, an exfoliant, a fungicide, a glosser, hair conditioner (hair conditioner agent), hair set resin, hair sheen agent, hair waving agent, a humectants (e.g., Erythritol, Homarine HCl, Ceratonia Siliqua (carob bean) gum), a moisturizer (e.g., sodium hyaluronate), an ointment base, a perfume, a protein, a skin calming agent, a skin cleanser, a skin conditioner (skin conditioning agent), a skin healing agent, a skin lightening agent, a skin protectant, a skin smoothing agent, a skin softening agent, a skin soothing agent, a sunscreen agent, a tanning accelerator, vitamins, a colorant, and a flavoring agent.

In some embodiments, the at least one additive is a sunscreen, such as Ethyl hexyl methoxycinnamate or titanium dioxide.

In some embodiments, each of the at least one effect-inducing additive may constitute between about 0.05 to 15% of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

The cosmetic or pharmaceutical compositions of the invention may also comprise pharmaceutical actives useful in the form of a chemical substance, material or compound, e.g., suitable for topical administration, to induce a desired local or systemic effect. Non-limiting examples of such actives are an antibiotic, an antiviral agent, an analgesic (e.g. ibuprofen, acetyl salicylic acid, naproxen, and the like), an antihistamine, an anti-inflammatory agent, an antipruritic, an antipyretic, an anesthetic agent, a diagnostic agent, a hormone, an antifungal agent, an antimicrobial agent, a cutaneous growth enhancer, a pigment modulator, an antiproliferative, an antipsoriatic, a retinoid, an anti-acne medicament (e.g. benzoyl peroxide, sulfur, and the like), an antineoplastic agent, a phototherapeutic agent, a keratolys (e.g. resorcinol, salicylic acid, and the like) and mixtures thereof.

Application of a composition of the invention onto the skin of a subject, for cosmetic/skin-care or therapeutic purposes may be in a single dose, in multiple doses, in a continuous or intermittent manner, depending, for example, upon the subject's physiological condition, whether the purpose of the administration is cosmetic or therapeutic/prophylactic and other factors known to the medical practitioner. The application of a composition of the invention may be essentially continuous over a pre-selected period of time or may be in a series of spaced doses.

The compositions of the invention are typically prepared by combining the ingredients of the active combination in appropriate concentrations. Other active or inert additives selected by one of skill in the art may optionally be added. The absolute weight of a given active agent included in a unit dose can vary widely. For example, about 0.1 microgram to about 5 g, or about 1 microgram to about 1 g, or about 10 microgram to about 500 mg, of at least one of the components can be administered by topical administration.

The compositions of the invention, being substantially for topical use, may be a skin-care formulation or a therapeutic formulation.

In some embodiments, the compositions of the invention are skin-care or dermo-pharmaceutical compositions (including, e.g., toiletries, health and beauty aids and cosmeceuticals) used for cosmetic and personal skin-care applications.

The term "cosmetic composition" or "skin care composition" relates to a composition of the invention that can be used for cosmetic purposes, purposes of hygiene or skincare or as a basis for delivery of one or more pharmaceutical ingredients. It is also possible that these compositions are used for two or more of these same purposes at one time. For example, a medicated dandruff shampoo may be used as a personal care product, i.e., to provide clean hair, and at the same time have pharmacological properties.

In some embodiments, the cosmetic compositions are for promoting bodily attractiveness, cover or mask the physical manifestations of a disorder or disease, modulate or alleviate wrinkling, unevenness and dryness in the skin of a mammal. The compositions additionally regulate skin condition and signs of skin aging (all perceptible manifestations as well as any other macro or micro effects) by regulating visible and/or tactile discontinuities in skin texture, including fine lines, wrinkles, enlarged pores, roughness and other skin texture discontinuities associated with aged skin with reduced irritation and dryness.

Thus, according to one of its aspect the present invention provides a composition (formulation) according to the invention for one or more of protecting and/or improving the state of the skin, and preventing and/or treating imperfections of the skin of a subject in need thereof.

According to another one of its aspect the present invention provides a composition (formulation) according to the invention for use in a method of one or more of protecting and/or improving the state of the skin, and preventing and/or treating imperfections of the skin of a subject in need thereof.

The invention further provides according to one of its aspect a method of one or more of protecting and/or improving the state of the skin, and preventing and/or treating imperfections of the skin of a subject in need thereof, said method comprising topically administering a composition according to the invention onto the skin of said subject.

In some embodiments, the method is used for treating rings under the eye, symptoms of aging, protecting the skin, increasing the detoxification of xenobiotics, intervening on pigmentation level, inhibiting melanogenesis, stimulating the detoxification systems, stimulating hair and body hair growth, modulating DHT levels, intervening on adipocytes, and promoting lipolysis.

In some embodiments, the method is used for rejuvenating the skin.

In some embodiments, the method is associate with non-medical condition of the skin.

In some embodiments, the method is associate with a medical condition of the skin.

In some embodiments, the method is for protecting and/or improving the state of the skin.

In some embodiments, the method is for preventing and/or treating imperfections of the skin of a subject.

In some embodiments, the compositions of the invention are for use in a method for protecting and/or improving the state of the skin.

In some embodiments, the compositions of the invention are for use in a method for preventing and/or treating imperfections of the skin of a subject.

In other embodiments, the compositions are pharmaceutical composition used in the treatment or prevention of at least one disease or disorder (e.g., of the skin).

In another aspect of the present invention, there is provided a use of at least one Dead Sea extract and at least one AoS extract for the preparation of a composition.

The compositions of the invention, in some embodiments, are formulated for use in the treatment of a disease or disorder.

Thus, the present invention also provides a method of therapeutic treatment or prophylaxis of such disease or disorder.

In some embodiments the disease or disorder is skin related.

In a further aspect, there is provided a method for treating a disease or disorder of the skin, the method comprising administering to a subject in need thereof a composition according to the invention.

In some embodiments the administration is topical administration.

In some embodiments, the subject is suffering, or has predisposition to suffer, or is one which may be exposed to conditions which increase the chances of suffering from a disease or disorder of the skin, which is optionally (may or may not be) related to one or more of age, sex, skin color, skin wounds, exposure to the sun, UV radiation, inflammation, irritation, a pre-existence of a disease not associated with the skin, etc.

In some embodiments, the disease or disorder of the skin is related to sun exposure.

In some embodiments, the disease or disorder of the skin is a secondary condition, e.g., inflammation, being related to an existing condition.

In some embodiments, the disease or disorder of the skin is skin irritation which may be related to an existing condition.

In further embodiments, the disease or disorder of the skin are age-related.

Non-limiting examples of such diseases or disorders of the skin are wounds, acne, psoriasis, atopic skin, diabetic skin, dermatitis, eczema, xerotic, dry skin, and chaffed skin.

In some embodiments, said administration is topical.

In a further one of its aspect the present invention provides compositions according to the invention for use in the treatment and/or prevention of one or more disease or disorder, the disease or disorder being associated with and/or being mediated by and/or being affected by and/or being related to one or more of biological pathways being selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof.

In another one of its aspects the present invention provides a method for treating and/or preventing of one or more disease and/or disorder, the method comprises administration of the composition (or any formulation thereof) according to the invention to a subject in need thereof, said disease or disorder being associated with and/or being mediated by and/or being affected by and/or being related to one or more of biological pathways beings selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof.

In some embodiments said disease or disorder may be associated with and/or mediated by and/or affected by and/or related to one or more of epithelial mesenchymal transition cellular pathway, glycolysis cellular pathway, MTORC1 signaling cellular pathway, TNFA signaling via NFKB pathway and hypoxia cellular pathway.

In some embodiments said disease or disorder may be associated with and/or mediated by and/or affected by and/or related to one or more of epithelial mesenchymal transition cellular pathway, glycolysis cellular pathway and hypoxia cellular pathway.

In some embodiments said disease or disorder may be associated with and/or mediated by and/or affected by and/or related to glycolysis cellular pathway and hypoxia cellular pathway.

In some embodiments said disease or disorder may be associated with and/or mediated by and/or affected by and/or related to epithelial mesenchymal transition cellular pathway.

In some embodiments said disease or disorder may be associated with and/or mediated by and/or affected by and/or related to glycolysis cellular pathway.

In some embodiments said disease or disorder may be associated with and/or mediated by and/or affected by and/or related to hypoxia cellular pathway.

In some embodiments said disease or disorder may be associated with and/or mediated by and/or affected by and/or related to MTORC1 signaling cellular pathway.

In some embodiments said disease or disorder may be associated with and/or mediated by and/or affected by and/or related to TNFA signaling via NFKB pathway.

In some embodiments in the method disclosed herein the administrations is topical administration onto (at least a region) the skin of the subject.

In some embodiments the compositions of the present invention may be used for selective treatment and/or prevention of specific one or more disease and/or disorder which may be associated with and/or mediated by and/or affected by and/or related to specific one or more of the above biological pathways. To this extent, the concentrations of each of the extracts (Dead Sea extract and AoS extract) in the combination may be optimized in order to achieve selective activity e.g., affecting specific one or more pathways while not affecting (or affecting to less extent) other one or more pathway/s.

Thus, in a further one of its aspects the present invention provides a method for selective treatment and/or prevention of one or more disease and/or disorder associated with and/or being mediated by and/or being affected by and/or being related to one or more of biological pathways beings selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof, the method comprises administration (e.g., topical) of the composition (or any formulation thereof) according to the invention to the subject (e.g., with the active ingredients concentrations and or relative concentrations being adjusted to achieve the selective treatment/prevention).

In some embodiments the selective treatment and/or prevention is specific to (one or more) disease and/or disorder associated with and/or being mediated by and/or being affected by and/or being related to epithelial mesenchymal transition cellular pathway, glycolysis cellular pathway, MTORC1 signaling cellular pathway, TNFA signaling via NFKB pathway and hypoxia cellular pathway.

In some embodiments the selective treatment and/or prevention is specific to (one or more) disease and/or disorder associated with and/or being mediated by and/or being affected by and/or being related to epithelial mesenchymal transition cellular pathway, glycolysis cellular pathway and hypoxia cellular pathway.

In some embodiments the selective treatment and/or prevention is specific to (one or more) disease and/or disorder associated with and/or being mediated by and/or being affected by and/or being related to glycolysis cellular pathway and hypoxia cellular pathway.

In some embodiments the selective treatment and/or prevention is specific to (one or more) disease and/or disorder associated with and/or being mediated by and/or being affected by and/or being related to glycolysis cellular pathway.

In some embodiments the selective treatment and/or prevention is specific to (one or more) disease and/or disorder associated with and/or being mediated by and/or being affected by and/or being related to hypoxia cellular pathway.

In some embodiments the selective treatment and/or prevention is specific to (one or more) disease and/or disorder associated with and/or being mediated by and/or being affected by and/or being related to MTORC1 signaling cellular pathway.

In some embodiments the selective treatment and/or prevention is specific to (one or more) disease and/or disorder associated with and/or being mediated by and/or being affected by and/or being related to TNFA signaling via NFKB pathway.

Non limiting disorders/diseases that may be associated with and/or mediated by and/or affected by and/or related to the adipogenesis cellular pathway are: cardiovascular diseases, interfering with insulin signaling by causing insulin resistance, which in turn leads to type 2 diabetes mellitus.

Non limiting disorders/diseases that may be associated with and/or mediated by and/or affected by and/or related to the androgen response cellular pathway are: Prostatic Neoplasms, Carcinoma, Papillary, Multiple Myeloma, Thyroid Neoplasms, Glioma, Osteosarcoma, Mouth Neoplasms, Insulin Resistance, Translocation, Genetic, Neoplasm Metastasis, Urinary Bladder Neoplasms, Neovascularization, Pathologic, Obesity, Melanoma, Adenocarcinoma, Ovarian Neoplasms, Lymphatic Metastasis, Stomach Neoplasms, Colonic Neoplasms, Carcinoma Squamous Cell, Cell Transformation, Neoplastic, Carcinoma, Pancreatic Neoplasms and Carcinoma Non-Small-Cell Lung.

Non limiting disorders/diseases that may be associated with and/or mediated by and/or affected by and/or related to the apoptosis cellular pathway are: Neoplasm Invasiveness, Colonic Neoplasms, Gingivitis, Carcinoma, Non-Small-Cell Lung, Ovarian Neoplasms, Stomach Neoplasms, Chronic Periodontitis, Parathyroid Neoplasms, Glioblastoma, Premature Birth, Lymphoma, Mantle-Cell, Systemic Inflammatory Response Syndrome, Carcinoma, Carcinoma Lobular and Tongue Neoplasms.

Non limiting disorders/diseases that may be associated with and/or mediated by and/or affected by and/or related to the complement cellular pathway are: Thrombophilia, Thrombosis, Thromboembolism, Hemolysis, Budd-Chiari Syndrome, Pregnancy Complications Hematologic, Venous Thromboembolism, Osteonecrosis Antiphospholipid Syndrome, Hemolytic-Uremic Syndrome, Hemophilia A and Choroidal Neovascularization.

Non limiting disorders/diseases that may be associated with and/or mediated by and/or affected by and/or related to DNA repair cellular pathway are: tumors formation and tumor heterogeneity.

Non limiting disorders/diseases that may be associated with and/or mediated by and/or affected by and/or related to the epithelial mesenchymal transition cellular pathway are: Ehlers-Danlos Syndrome, Fibrosis, Muscular Dystrophies, Neoplasm Metastasis, Premature Birth, Marfan Syndrome and Aneurysm, Dissecting.

Non limiting disorders/diseases that may be associated with and/or mediated by and/or affected by and/or related to the estrogen response early cellular pathway are: Carcinoma Lobular, Salivary Gland Neoplasms, Lymphoma, Follicular, Precursor T-Cell Lymphoblastic Leukemia-Lymphoma, Hearing Loss, Deafness, Neoplasms, Hormone-Dependent, Neoplasm Invasiveness, Hearing Loss Sensorineural, Mesothelioma, Leukemia Promyelocytic Acute, Translocation Genetic, Carcinoma Papillary, Neoplasms Glandular and Epithelial, Nasopharyngeal Neoplasms, Laryngeal Neoplasms, Carcinoma Ductal Breast, Endometrial Neoplasms, Lymphoma Large B-Cell Diffuse, Mouth Neoplasms, Precancerous Conditions, Leukemia Lymphocytic, Chronic B-Cell, Carcinogenesis and Multiple Myeloma.

Non limiting disorders/diseases that may be associated with and/or mediated by and/or affected by and/or related to the estrogen response late cellular pathway are: Osteochondrodysplasias, Salivary Gland Neoplasms, Carcinoma, Papillary, Hearing Loss, Laryngeal Neoplasms, Nasopharyngeal Neoplasms, Hearing Loss, Sensorineural, Carcinoma, Transitional Cell, Neoplasm Invasiveness, Carcinoma, Squamous Cell, Cystic Fibrosis, Carcinoma Ductal Breast, Carcinoma, Myelodysplastic Syndromes Mouth Neoplasms, Neoplasms, Glandular and Epithelial, Precancerous Conditions, Translocation, Genetic, Thyroid Neoplasms, Lymphoma Large B-Cell Diffuse, Lymphatic Metastasis, Inflammatory Bowel Diseases, Endometrial Neoplasms, and Precursor Cell Lymphoblastic Leukemia-Lymphoma.

Non limiting disorders/diseases that may be associated with and/or mediated by and/or affected by and/or related to the glycolysis cellular pathway are: Ehlers-Danlos Syndrome, Small Cell Lung Carcinoma, Chondrosarcoma, Genetic Diseases X-Linked, Cholangiocarcinoma, Nasopharyngeal Neoplasms, Neovascularization Pathologic, Bile Duct Neoplasms, Laryngeal Neoplasms, Carcinoma, Pancreatic Ductal Carcinogenesis, Neoplasms, Glandular and Epithelial, Bone Neoplasms, Neoplasm Metastasis, Abnormalities Multiple, Carcinoma Ductal Breast, Osteosarcoma, Glioblastoma, Hypoxia, Mouth Neoplasms, Lymphatic Metastasis, Neoplasm Invasiveness, Carcinoma Renal Cell and Carcinoma.

Non limiting disorders/diseases that may be associated with and/or mediated by and/or affected by and/or related to the heme-metabolism cellular pathway are Hematologic disorders, such as anemias and porphyrias and erythropoietic diseases.

Non limiting disorders/diseases that may be associated with and/or mediated by and/or affected by and/or related to the hypoxia cellular pathway are: Neovascularization Pathologic and peroxisome biogenesis disorders.

Non limiting disorders/diseases that may be associated with and/or mediated by and/or affected by and/or related to the interferon alpha response cellular pathway are: Hepatitis C, Hepatitis B Chronic, HIV Infections, Diabetes Mellitus Type 1, Inflammation, Lupus Erythematosus Systemic, Multiple Sclerosis, Arthritis Rheumatoid, Disease Progression, Genetic Predisposition to Disease, and Breast Neoplasms.

Non limiting disorders/diseases that may be associated with and/or mediated by and/or affected by and/or related to the interferon gamma response cellular pathway are: Hepatitis B Chronic, Hepatitis C, Chronic, Inflammation and Thyroiditis Autoimmune.

Non limiting disorders/diseases that may be associated with and/or mediated by and/or affected by and/or related to the MTORC1 signaling cellular pathway are: Anemia, Hemolytic, Congenital Nonspherocytic.

Non limiting disorders/diseases that may be associated with and/or mediated by and/or affected by and/or related to the MYC targets V1 cellular pathway are: Myelodysplastic Syndromes, Laryngeal Neoplasms, HIV Infections, Nasopharyngeal Neoplasms, Genomic Instability, Osteosarcoma, Translocation Genetic, Leukemia Myeloid Acute, Carcinogenesis, Leukemia, Mouth Neoplasms, Lupus Erythematosus Systemic, Cell Transformation Neoplastic, Neuroblastoma, Carcinoma Non-Small-Cell Lung, Amyotrophic Lateral Sclerosis, Parkinson Disease, Glioblastoma, Colonic Neoplasms, Carcinoma Squamous Cell, Melanoma, Pancreatic Neoplasms, Carcinoma Hepatocellular and Stomach Neoplasms.

Non limiting disorders/diseases that may be associated with and/or mediated by and/or affected by and/or related to the oxidative phosphorylation cellular pathway are: Paraganglioma and Leigh Disease.

Non limiting disorders/diseases that may be associated with and/or mediated by and/or affected by and/or related to the P53 cellular pathway are: Xeroderma Pigmentosum.

Non limiting disorders/diseases that may be associated with and/or mediated by and/or affected by and/or related to the protein secretion cellular pathway are: Neuroblastoma, Melanoma, Pancreatic Neoplasms, Carcinoma, Non-Small-Cell Lung, Alzheimer Disease, Neoplasm Metastasis, Stomach Neoplasms, HIV Infections, Cell Transformation Neoplastic, Carcinoma Hepatocellular, Colorectal Neoplasms, Carcinoma Squamous Cell, Liver Neoplasms, Neoplasm Invasiveness, Adenocarcinoma, Prostatic Neoplasms, Disease Progression, Genetic Predisposition to Disease and Breast Neoplasms.

Non limiting disorders/diseases that may be associated with and/or mediated by and/or affected by and/or related to the TNFA signaling via NFKB cellular pathway are: Atherosclerosis, Chronic Periodontitis, Gingivitis, AIDS Dementia Complex, Periodontitis and Pre-Eclampsia.

Non limiting disorders/diseases that may be associated with and/or mediated by and/or affected by and/or related to the unfolded protein response cellular pathway are: Breast Neoplasms, Carcinoma, Hepatocellular, Carcinoma Non-Small-Cell Lung, Carcinoma Squamous Cell, Cell Transformation Neoplastic, Colonic Neoplasms, Colorectal Neoplasms, Diabetes Mellitus Type 2, Disease Progression, Genetic Predisposition to Disease, HIV Infections, Liver Neoplasms, Lung Neoplasms, Lymphatic Metastasis, Multiple Myeloma, Neoplasm Invasiveness, Neoplasm Metastasis, Neoplasms, Neovascularization Pathologic, Parkinson Disease, Prostatic Neoplasms and Translocation Genetic.

In some embodiments the compositions of the present invention affect the epithelial mesenchymal transition biological pathway via increase of fibronectin production e.g., as a result of topical application onto the skin.

In some embodiments the compositions of the present invention affect the glycolysis biological pathway via increase of expression of phosphofructokinase e.g., as a result of topical application onto the skin.

In some embodiments the compositions of the present invention affect the hypoxia biological pathway via increase of expression of hypoxia inducible factor 1 e.g., as a result of topical application onto the skin.

In some embodiments the compositions of the present invention beneficially affect the skin via increase of fibronectin production.

In some embodiments the compositions of the present invention beneficially affect the skin via increase of expression of phosphofructokinase.

In some embodiments the compositions of the present invention beneficially affect the skin via increase of expression of hypoxia inducible factor 1.

In some embodiments the compositions of the present invention beneficially affect the skin via affecting one or more cellular biological mechanisms (e.g., by reducing the damage of the cellular natural processes).

In some embodiments the compositions of the present invention beneficially affect the skin via coping with stress.

In some embodiments the compositions of the present invention beneficially affect the skin via optimizing cellular metabolic balance and regeneration.

In some embodiments the compositions of the present invention beneficially affect the skin via affecting cellular energy production.

In some embodiments the compositions of the present invention beneficially affect the skin via skin energy enhancement at a cellular level.

In some embodiments the compositions of the present invention beneficially affect the skin via skin calming at a cellular level.

In some embodiments the compositions of the present invention beneficially affect the skin via resistance to hypoxia.

In some embodiments the compositions of the present invention beneficially affect the skin via affecting one or more gene-expression and/or one or more protein expression.

In some embodiments the compositions of the present invention beneficially affect the skin at the molecular level e.g., by affecting (e.g., enhancing or reducing) the expression of one or more molecules that are involved in skin related conditions.

In some embodiments the compositions of the present invention may be used for wound healing.

In some embodiments the compositions of the present invention may be used for the treatment of infection of the skin.

The term "topical" as used herein above and below refers to the application of a composition according to the invention directly onto at least a portion of a subject's skin (human's or non-human's skin) so as to achieve a desired effect, e.g., cosmetic or therapeutic effect, at the site of application. In some embodiments, the desired effect is achieved at the site of application without inducing one or more systemic effects. In other embodiments, the formulation of the invention induces at least a partial systemic effect which contributes to the induction of at least one desired effect.

The term "skin" as used herein above and below refers to any part of the human or animal skin, including the whole surface thereof, hair and nails.

The term "treatment" as used herein above and below refers to administration (e.g., topical) of an effective amount of a composition of the present invention effective to ameliorate undesired symptoms associated with a disease/disorder (e.g., skin disease), to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

In some embodiments the disease and/or disorder is a non-medical condition e.g., associated with normal skin conditions.

In some embodiments the disease and/or disorder is a medical condition e.g., associate with pathological skin conditions.

The "effective amount", whether a therapeutically or cosmetically effective amount for purposes herein, is determined by such considerations as may be known in the art. The amount must be effective to achieve one or more of the above desired therapeutic or cosmetic effects, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile, a variety of pharmacological parameters such as half-life on the skin, on undesired side effects, if any, on factors such as age and gender, etc.

As used herein above and below the term "about" refers to ±10% of the indicated value.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

As used herein, the singular form "a", "an" and "the" include plural references unless the context clearly dictates otherwise. For example, the term "an extract" or "at least one extract" may independently include a plurality of extracts, including a variety thereof.

Various embodiments and aspects of the present invention as delineated hereinabove and as claimed in the claims section below find experimental support in the following examples.

The following embodiments are non-limiting exemplary embodiments according to the present invention:

Embodiment 1: A composition comprising at least one Dead Sea extract and at least one extract of the Apple of Sodom (*Calotropis procera*).

Embodiment 2: The composition according to Embodiment 1, wherein said Dead Sea extract is a mixture of natural materials obtained from the waters of the Dead Sea, the mud surrounding the Dead Sea and/or the soil bed of the Dead Sea.

Embodiment 3: The composition according to Embodiment 1, wherein said Dead Sea extract is the saline waters obtained from the Dead Sea.

Embodiment 4: The composition according to Embodiment 3, wherein the Dead Sea water has a specific density of 1.25-1.35 g/ml, pH of 4.6-5.6 (at 25° C.), and less than 100 cfu/g of non-pathogenic microbes.

Embodiment 5: The composition according to any one of Embodiments 2 to 4, wherein the Dead Sea water comprises $Ca^{+2}$, $Cl^-$, $Mg^{+2}$, $Na^+$, $K^+$ and $Br^-$.

Embodiment 6: The composition according to Embodiment 1, wherein said Dead Sea extract is a an aqueous solution simulating the salts and minerals content of the Dead Sea water.

Embodiment 7: The composition according to any one of Embodiments 1 to 6, wherein said at least one extract of the Apple of Sodom (*Calotropis procera*) is obtained from one or more of the AoS roots, leaves, leaf blades, seeds, stems, fruits, shoot and barks (peel).

Embodiment 8: The composition according to any one of Embodiments 1 to 7, wherein said at least one extract of the Apple of Sodom (*Calotropis procera*) is obtained from a cell culture of callus induced from one or more of the AoS roots, leaves, leaf blades, seeds, stems, fruits, shoot and barks (peel).

Embodiment 9: The composition according to any one of Embodiments 1 to 8, wherein said at least one extract of the Apple of Sodom (*Calotropis procera*) is obtained from a cell culture of the AoS leaves.

Embodiment 10: The composition according to any one of Embodiments 1 to 6, wherein said at least one extract of the Apple of Sodom (*Calotropis procera*) is obtained from the AoS whole plant.

Embodiment 11: The composition according to any one of Embodiments 1 to 10, wherein said at least one extract of the Apple of Sodom (*Calotropis procera*) is an ex-vitro plant extract.

Embodiment 12: The composition according to any one of Embodiments 1 to 10, wherein said at least one extract of the Apple of Sodom (*Calotropis procera*) is an ex-vitro explant extract.

Embodiment 13: The composition according to any one of Embodiments 1 to 12, wherein said at least one extract of the Apple of Sodom (*Calotropis procera*) is an extract of in vitro plantlets callus. Embodiment 14: The composition according to Embodiment 13, wherein said at least one extract of the Apple of Sodom (*Calotropis procera*) is an extract of in vitro plantlets leaves.

Embodiment 15: The composition according to any one of Embodiments 1 to 14, wherein said at least one extract of the Apple of Sodom (*Calotropis procera*) is a non-toxic extract.

Embodiment 16: The composition according to Embodiment 15, wherein said at least one extract of the Apple of Sodom (*Calotropis procera*) is substantially free of the Calotropin toxin.

Embodiment 17: The composition according to any one of Embodiments 1 to 16, wherein said at least one extract of the Apple of Sodom (*Calotropis procera*) is from AoS originated from the Dead Sea area.

Embodiment 18: The composition according to any one of Embodiments 1 to 17, wherein said at least one extract of the Apple of Sodom (*Calotropis procera*) is an aqueous extract.

Embodiment 19: The composition according to any one of Embodiments 1 to 18, wherein said at least one extract of the Apple of Sodom (*Calotropis procera*) is an aqueous extract substantially free of an organic solvent.

Embodiment 20: The composition according to Embodiment 19, wherein said organic solvent is one or more of petroleum ether, methanol and chloroform.

Embodiment 21: The composition according to any one of Embodiments 1 to 20, wherein said at least one extract of the Apple of Sodom (*Calotropis procera*) is a pure (neat) extract or an extract formulated with at least one additive.

Embodiment 22: The composition according to Embodiment 21, wherein said additive is a stabilizer, a diluent, a carrier, a filler, an antioxidant or any other inert additive.

Embodiment 23: The composition according to Embodiment 21, wherein said additive is glycerol.

Embodiment 24: The composition according to any one of Embodiments 1 to 23, wherein said at least one extract of the Apple of Sodom (*Calotropis procera*) is an extract as herein described and exemplified.

Embodiment 25: The composition according to any one of Embodiments 1 to 23, wherein said at least one Dead Sea extract is an extract as herein described and exemplified.

Embodiment 26: The composition of any one of the Embodiments 1 to 25, being a composition selected from a skin-care and pharmaceutical composition.

Embodiment 27: The composition according to Embodiment 26, wherein said composition is for topical application.

Embodiment 28: The composition according to Embodiment 27, being a synergistic composition.

Embodiment 29: The composition according to any one of Embodiments 1 to 28, being in the form selected from a lotion, an ointment, a gel, a mask, a toner, an essence, a cream, a water in oil or oil in water emulsion, a shampoo, a moisturizer, a sunscreen, a cream, a stick, a spray, an aerosol, foam, a paste, a mousse, a solid, semi-solid, or a liquid make-up, a foundation, and an eye make-up.

Embodiment 30: The composition according to any one of Embodiments 1 to 29, further comprising at least one additive selected from a diluent, a preservative, an abrasive, an anticaking agent, an antistatic agent, a binder, a buffer, a dispersant, an emollient, an emulsifier, a co-emulsifiers, a fiberous material, a film forming agent, a fixative, a foaming agent, a foam stabilizer, a foam booster, a gellant, a lubricant, a moisture barrier agent, a plasticizer, a preservative, a propellant, a stabilizer a surfactant, a suspending agent, a thickener, a wetting agent, and a liquefier.

Embodiment 31: The composition according to any one of Embodiments 1 to 30, further comprising at least one additive selected from an anti-acne agent, an anti-aging agent, an antibacterial agent, an anti-cellulites agent, an antidandruff agent, an antifungal agent, an anti-inflammatory agent, an anti-irritation agent, an antimicrobial agent, an antioxidant agent, an antiperspirant agent, an antiseptic agent, a cell stimulant, a cleansing agent, a conditioner, a deodorant, a depilatory, a detergent, an enzyme, an essential oil, an exfoliant, a fungicide, a glosser, hair conditioner, hair set resin, hair sheen agent, hair waving agent, a humectants, a moisturizer, an ointment base, a perfume, a protein, a skin calming agent, a skin cleanser, a skin conditioner, a skin healing agent, a skin lightening agent, a skin protectant, a skin smoothing agent, a skin softening agent, a skin soothing agent, a sunscreen agent, a tanning accelerator, vitamins, a colorant, and a flavoring agent.

Embodiment 32: The composition according to any one of Embodiments 1 to 25 for use in the preparation of a cosmetic/skin-care or pharmaceutical composition.

Embodiment 33: The composition according to Embodiment 32, wherein said composition is for protecting and/or improving the state of the skin, preventing and/or treating imperfections of the skin of a subject.

Embodiment 34: The composition according to Embodiment 33, wherein the composition is for treating rings under the eye, symptoms of aging, protecting the skin, increasing the detoxification of xenobiotics, intervening on pigmentation level, inhibiting melanogenesis, protecting the body against pollution, stimulating the detoxification systems, stimulating hair and body hair growth, modulating DHT levels, intervening on adipocytes, and/or promoting lipolysis.

Embodiment 35: The composition according to Embodiment 32, wherein said composition is for treating or preventing at least one disease or disorder of the skin.

Embodiment 36: The composition according to Embodiment 35, wherein said disease or disorder of the skin is a secondary condition, being related to an existing condition.

Embodiment 37: The composition according to Embodiment 36, wherein said secondary condition is inflammation.

Embodiment 38: A lotion, an ointment, a gel, a mask, a toner, an essence, a shampoo, a moisturizer, a sunscreen, a cream, a stick, a spray, an aerosol, foam, a paste, a mousse, a solid, semi-solid, or a liquid make-up, a foundation, or an eye make-up comprising a composition according to any one of Embodiments 1 to 25.

Embodiment 39: The composition according to any one of Embodiments 1 to 25 for use in the treatment and/or prevention of one or more disease or disorder, wherein said disease or disorder is associated with and/or is mediated by and/or is affected by and/or is related to one or more of biological pathways beings selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof.

Embodiment 40: The composition for use according to Embodiment 39, wherein said cellular pathway is one or more of epithelial mesenchymal transition, glycolysis and hypoxia.

Embodiment 41: The composition for use according to Embodiment 39, wherein said cellular pathway is glycolysis and hypoxia cellular pathway.

Embodiment 42: The composition for use according to Embodiment 39, wherein said cellular pathway is epithelial mesenchymal transition.

Embodiment 43: The composition for use according to Embodiment 39, wherein said cellular pathway glycolysis.

Embodiment 44: The composition for use according to Embodiment 39, wherein said cellular pathway hypoxia.

Embodiment 45: The composition for use according to Embodiment 39, wherein said disease or disorder is skin inflammation and/or skin irritation.

Embodiment 46: The composition according to any one of Embodiments 1 to 25 for use in a method of protecting and/or improving the state of the skin of a subject, preventing and/or treating imperfections of the skin of a subject in need thereof, said method comprising topically administering a composition according to any one of Embodiments 1 to 25 onto the skin of said subject.

Embodiment 47: The composition for use according to Embodiment 46, for treating rings under the eye, symptoms of aging, protecting the skin, increasing the detoxification of xenobiotics, intervening on pigmentation level, inhibiting melanogenesis, protecting the body against pollution, stimulating the detoxification systems, stimulating hair and body hair growth, modulating DHT levels, intervening on adipocytes, and/or promoting lipolysis. Embodiment 48: The composition according to any one of Embodiments 1 to 25 for use in a method for treating or preventing a disease or disorder of the skin of a subject, said method comprising administering to a subject in need thereof a composition according to any one of Embodiments 1 to 25.

Embodiment 49: The composition for use according to Embodiment 48, wherein said disease or disorder of the skin is a secondary condition, being related to an existing condition or inflammation.

Embodiment 50: A method for treating and/or preventing one or more disease or disorder, the method comprises administration of the composition according to any one of Embodiments 1 to 25 to a subject in need thereof, wherein said disease or disorder is associated with and/or is mediated by and/or is affected by and/or is related to one or more of biological pathways beings selected from adipogenesis cellular pathway, androgen response cellular pathway, apoptosis cellular pathway, complement cellular pathway, DNA repair cellular pathway, epithelial mesenchymal transition cellular pathway, estrogen response early cellular pathway, estrogen response late cellular pathway, glycolysis cellular pathway, heme-metabolism cellular pathway, hypoxia cellular pathway, interferon alpha response cellular pathway, interferon gamma response cellular pathway, MTORC1 signaling cellular pathway, MYC targets V1 cellular pathway, oxidative phosphorylation cellular pathway, P53 cellular pathway, protein secretion cellular pathway, TNFA signaling via NFKB cellular pathway, unfolded protein response cellular pathway and any combination thereof.

Embodiment 51: The method according to Embodiment 50, wherein said cellular pathway is one or more of epithelial mesenchymal transition, glycolysis and hypoxia.

Embodiment 52: The method according to Embodiment 50, wherein said cellular pathway is glycolysis and hypoxia cellular pathway.

Embodiment 53: The method according to Embodiment 50, wherein said cellular pathway is epithelial mesenchymal transition.

Embodiment 54: The method according to Embodiment 50, wherein said cellular pathway glycolysis. Embodiment 55: The method according to Embodiment 50, wherein said cellular pathway hypoxia.

Embodiment 56: The method according to Embodiment 50, wherein said disease or disorder is skin inflammation and/or skin irritation.

DETAILED DESCRIPTION OF EMBODIMENTS

The following examples are not in any way intended to limit the scope of the invention as claimed.

Example 1: Dead Sea Extract

In the present disclosure a commercial preparation of a Dead Sea extract referred to herein as "Osmoter" or "Osmoter™" or "Mineral Skin Osmoter" was used. The preparations is also known as "Maris Sal" or "Maris Aqua" (Dead Sea Water, DSW) (Source: Geological Survey—Ministry of National Infrastructures, State of Israel, especially for AHAVA-Dead Sea Laboratories CAS # INCI Monograph ID:11089).

The "Osmoter" solution has the following composition:

| | Salt normality (N) |
|---|---|
| Na | 0.118 (2.720 g/l) |
| K | 0.054 (2.100 g/l) |
| Ca | 0.873 (35.000 g/l) |
| Mg | 3.815 (92.700 g/l) |
| Ba | $6.6 \times 10^{-5}$ (0.009 g/l) |
| Cd | $<1.8 \times 10^{-7}$ ($<2 \times 10^{-5}$ g/l) |
| Co | $<3.4 \times 10^{-5}$ (<0.002 g/l) |
| Cu | $<3.15 \times 10^{-5}$ (<0.004 g/l) |
| Cr | $<3.85 \times 10^{-4}$ (<0.02 g/l) |
| Fe | $<3.58 \times 10^{-5}$ (<0.002 g/l) |
| Li | $5.76 \times 10^{-3}$ (0.040 g/l) |
| Mn | $1.82 \times 10^{-4}$ (0.010 g/l) |
| Mo | $<1.04 \times 10^{-6}$ ($<10^{-4}$ g/l) |
| Ni | $<3.4 \times 10^{-5}$ (<0.002 g/l) |
| Pb | $<9.6 \times 10^{-8}$ ($<2 \times 10^{-5}$) |
| Rb | $3.5 \times 10^{-6}$ ($<3 \times 10^{-4}$ g/l) |
| Sb | $<1.6 \times 10^{-7}$ ($<2 \times 10^{-5}$ g/l) |
| Sr | $7.6 \times 10^{-3}$ (0.670 g/l) |
| V | $<7.9 \times 10^{-5}$ (<0.004 g/l) |
| Th | $<8.6 \times 10^{-8}$ ($<2 \times 10^{-5}$ g/l) |
| U | $<8.4 \times 10^{-8}$ ($<2 \times 10^{-5}$ g/l) |
| Zn | $<3.06 \times 10^{-5}$ (<0.002 g/l) |
| Cl | 9.75 (346 g/l) |
| Br | 0.175 (14 g/l) |
| B | 0.011 (0.120 g/l) |
| As | $2.7 \times 10^{-5}$ (0.002 g/l) |

-continued

| | Salt normality (N) |
|---|---|
| I | $6.30 \times 10^{-7}$ ($8 \times 10^{-8}$ g/l) |
| SiO2 | $<3.33 \times 10^{-4}$ (<0.02 g/l) |
| SiO4 | $<2.2 \times 10^{-3}$ (<0.2 g/l) |

Solutions comprising Dead Sea Water were prepared by dilutions of the "Osmoter" preparation (See below). Various concentrations of the "Osmoter" preparation were used i.e., 0.1%, and 0.5% (w/w).

It is noted that the percentages of the Dead Sea extract in the compositions of the present disclosure are provided herein above and below in weight per weight ratio (w/w) i.e., the weight in grams of the Dead Sea extract (e.g., Osmoter) per 100 gram total weight of the composition.

Example 2: AoS Extracts

In the present disclosure the AoS extract was prepared by Evonik Advanced Botanicals.

2.1. Cell Suspensions of *Calotropis procera*

2.1.1 In Vitro Establishment

Sources of plant material were provided from the Dead Sea area by AHAVA.

Several protocols were tested to obtain aseptic cultures of *Calotropis procera*. The best results were achieved with the protocol consisted of 70% ethanol (3 min) followed by 2.6% NaCLO (30 min).

From the different sources of plant material only stems were not sterilized and consequently this plant material was not used in the screening of induction media.

2.1.2 Callus Induction

Leaf and flower explants from *Calotropis procera* ex vitro plants as well epicotyls from in vitro-grown plantlets have been used as explants for the induction of callus.

Three different cytokinins (TDZ, BAP or Kinetin) at three different concentrations combined with an auxin (NAA) at different concentrations were tested with ex vitro explants.

2.1.2.1 In Vitro Explants

Different organs were excised from in vitro plantlets (cotyledons, epicotyl, hypocotyl, and $1^{st}$ and $2^{nd}$ leaf). For all explants three different media have been tested and callus induction and root formation was determined (Table 1). Best results in terms of callus friability was obtained using Murashige and Skoog (MS) supplemented with naphthalene acetic acid (NAA).

TABLE 1

Combinations used with *Calotropis procera* leaf explants for callus induction.

| Hormone combination (mg/L) | Explant | Callus formation | Root formation (from callus) |
|---|---|---|---|
| 1 KIN + 0.5 NAA (CPI) | Cotyledons | + | − |
| | Epicotyle | ++ | + |
| | Hypocotyle | ++ | + |
| | $1^{st}$ and $2^{nd}$ leaves | − | + |

TABLE 1-continued

Combinations used with *Calotropis procera* leaf explants for callus induction.

| Hormone combination (mg/L) | Explant | Callus formation | Root formation (from callus) |
|---|---|---|---|
| 0.1 TDZ + 3 NAA (CP2) | Cotyledons | + | − |
| | Epicotyle | ++ | − |
| | Hypocotyle | ++ | − |
| | 1$^{st}$ and 2$^{nd}$ leaves | − | − |
| 0.1 TDZ + 5 NAA (J1) | Cotyledons | + | − |
| | Epicotyle | ++ | − |
| | Hypocotyle | ++ | − |
| | 1$^{st}$ and 2$^{nd}$ leaves | − | − |

2.1.3 Cell Suspensions

According to previous results, cell suspensions were established using the above noted CP1, CP2 and J1 media.

2.1.4 Secondary Metabolite Analysis

FIG. 1 represents the HPLC profiles of leaf ethanolic extracts from in vitro and ex-vitro cultures (the tested samples were obtained by extraction of 50 mg dry weight (DW) in 1.5 ml 70% ethanol, 1 night in container at 25° C. under orbital agitation followed by centrifugation of 10 min at 13000 rpm and resuspension in 0.25 mL 80% MeOH (concentration×4). The rest was filtered using 0.45 μm filter for raw extracts. The HPLC was conducted on column Luna C18 (250×4.6, 5μm), injection volume of 20 μl, at a flow rate of 0.7 ml/min and detection at 220 nm. The solvents used were ultrapure water and acetonitrile (ACN) (75% water and 25% ACN at time 0 and 4, 50% water and 50% ACN at time 24, 30% water and 70% ACN at time 29, 0% water and 100% ACN at times 31 and 41 and 75% water and 25% ACN at time 43.

Ex vitro and in vitro plants profiles were similar but different (FIG. 1). As can be noted from FIG. 1, most of the peaks are common to both extract.

The major peak identified from leaves by HPLC and displaying a typical absorbance of cardenolides was subjected to fractionation and was analyzed by mass spectrometry (Ultra-High Pressure Liquid Chromatography-Triple Quadrupole Detector) in positive and negative modes by electron spray ionization. The molecular weight of this compound was determined as 587.7 Da (FIGS. 2A-2D). From these data it was conclude that Uscharin is the major constituent of the ethanolic extract of the leaves of *Calotropis procera*.

2.2. *Calotropis procera* Cell Culture

2.2.1 Scale Up

The scale up was done progressively from Erlenmeyer flasks of different volumes (100 mL, 250 mL, 500 mL and 1000 mL). Once the growth rate was demonstrated to be stable, the production was started in wave bioreactors. All the parameters checked in the biomass scale up (colour, odour and growth rate) were stable.

2.2.2 Plant Extraction

Two kinds of extracts (i.e. ethanol and aqueous) were developed. Both extracts were developed with the help of a soxhlet for 3 hours. The solvent for the ethanolic extract consisted of 70% ethanol:30% water and 100% water in the case of the aqueous extract. Both extracts were analyzed by HPLC showing some differences mainly in peak levels (data not shown).

2.2.3 Chemical Analysis

The metabolic analysis of cell suspension extracts was performed in a first step by HPLC. The analysis of both extracts showed very similar profiles and the presence of calotropine was not detected. The identification of main peaks was carried out by MS.

In the preliminary analysis, a mass corresponding to 520 could be identified to different isomers of asclepioside as detailed herein below.

Figure 3:
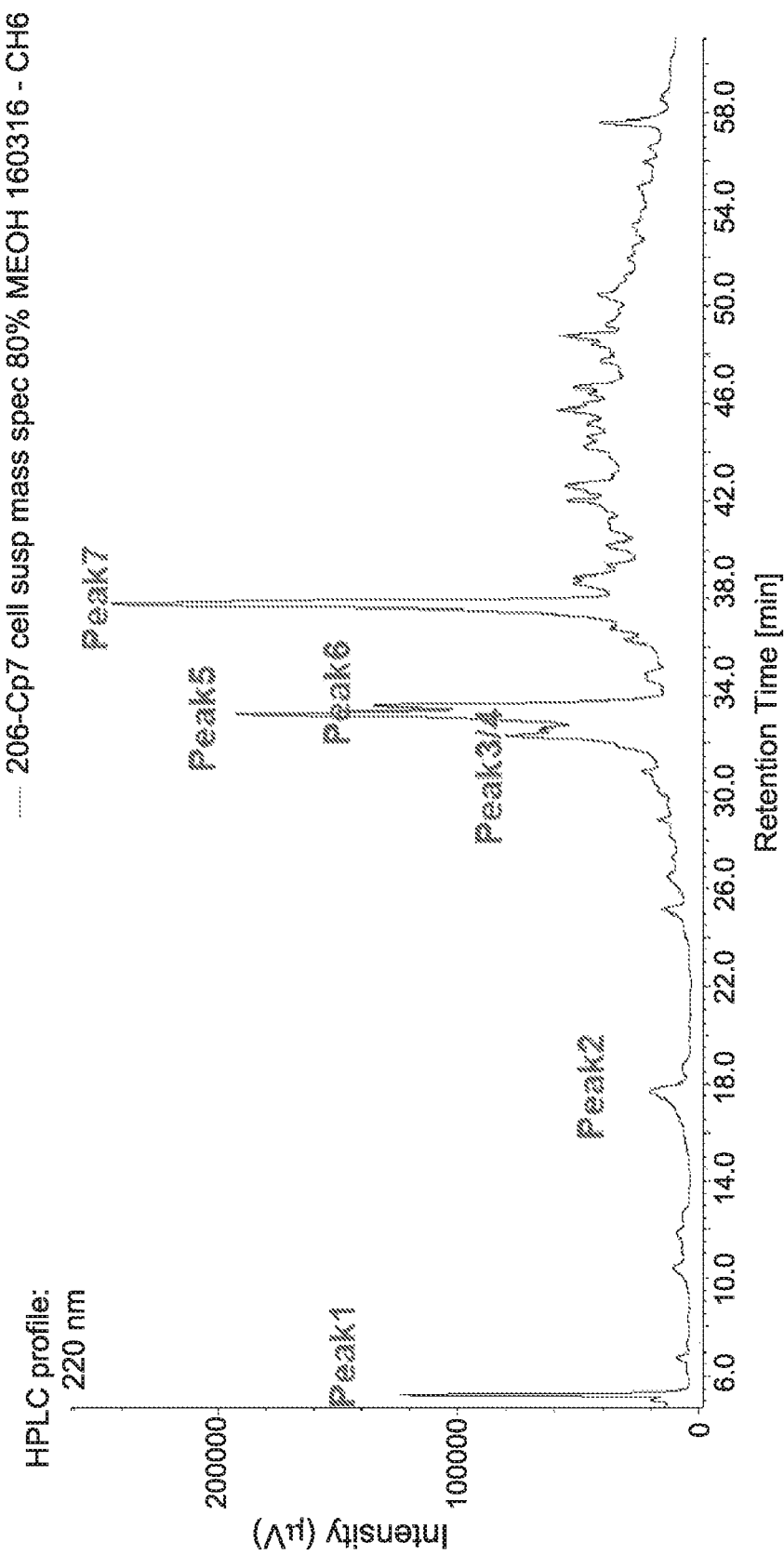
FIG. 3 represents the HPLC profil of undifferentiated cells extract from AoS according to some embodiments of the invention.

Undifferentiated cells from *C. procera* were analyzed by HPLC (FIG. 3). Acquity UPLC-TQD (Ultra High Pressure Liquid Chromatography-Triple Quadrupole Detector) equipment from Waters was used with Luna column C18 (2)-HST (100×2.0 mm, 2.5 μm), with injection volume of 7.5 μL, flow rate of 0.6 ml/min and with eluting solution of water and ACN (each including 1% formic acid).

As indicated in FIG. 3, the global metabolite profile is different (compared to FIG. 1), with a lower intensity. In fact, most peaks in undifferentiated cells do not reach an intensity of 200 000 uV, whereas several peaks reached over 400 000 uV in leaf extracts. Globally, yields were 3× lower in undifferentiated cells that in leaves extracts. On top of that, the most abundant peak in the leaves, eluting at 30.5 min, Uscharin, is not present in the undifferentiated extract. The only common compound present in both leaves and undifferentiated cells of *Calotropis procera* is the unknown molecule eluting at 38 min, with a molecular mass of 700 Da, which is not corresponding to any of the toxic compounds identified so far in calotropis.

It is noted in this respect that previously identified toxic compounds from calotropis plant species, along with their molecular mass are Calotropin (523,63 Da), Calactin (523,63 Da), Calotoxin (548,63 Da), Uscharidin (530,61 Da), Calotropagenin (404,50 Da), Uscharin (587,67 Da), Gigantin (154,12 Da), 3'O acetyl calotropin (synonyme of asclepin, 574,67 Da), Calotropin 3' glucoside (694,77 Da), Calotropone (468,59 Da), Calotroposide A and B (1189,44 Da and 1205,44 Da), Frugoside (536,66 Da), Proceroside (548,63 Da), Uzarigenin (374,52 Da), Voruscharin (589,74 Da) and 2'Oxovoruscharin (603,73 Da) [1]).

The most abondant compounds, eluding between 32 and 33 min in FIG. 3 were identified as a molecule with a molecular mass of 520 Da. The same compound appears to be also detected in Calotropis gigantea callus culture, in agreement with Tripathi et al. [17].

The compound eluting at 38min with a Mass of 700 Da was not identified.

The following mass spectrometry was performed on the undifferentiated cell extracts of *Calotropis procera*:

TABLE 2

Identification of main peaks from cells - synthesis of mass data

| Peak | UV λmax (nm) | [M + H]⁺ m/z 30 eV | [M + H]⁺ m/z 60 eV | [M − H]⁻ m/z 30 eV | [M − H]⁻ m/z 60 eV | MW | Assigned identity (hypotheses) |
|---|---|---|---|---|---|---|---|
| 1-5 min | 216; 260 | — | — | — | — | — | — |
| 2-17.5 min | 220; 250; 330 | 501*; 185 (478 + 22 + 1)* | 501*; 185 (478 + 22 + 1)* | 477; 955* (478 × 2 − 1) | 477; 445; 955* (478 × 2 − 1) | 478 | — |
| 3 & 4 32 & 32.5 min | 220; 277 | 503; 543* (520 + 22 + 1) | 503 | 565*; 339 (520 + 46 − 1)* | | 520 | Unknon Asclepioside |
| 5-33 min | 221; 276 | 503; 543* (520 + 22 + 1) | 503; 543*; 323; 311 (520 + 22 + 1) | 565*; 1085** (520 + 46 − 1)* (520 × 2 + 46 − 1)** | 339 | 520 | Unknown Asclepioside |
| 6-33.5 min | 221; 276 | 503; 543* (520 + 22 + 1) | 503 | 565*; 519 (520 + 46 − 1)* | 339 | 520 | Unknown Asclepioside |
| 7-37.5 min | 221; 276 | 701; 679 | 701; 679; 340 | 745* (700 + 46 − 1)* | 745; 1491 (746 × 2 − 1) | 700 | — |

*+22: sodium adduct (residues from MeOH), +46: formic acid adduct
MW: molecular weight Each of the above noted peak was analyzed in positive and negative modes by electron spray ionization (data not shown). From these data, it was possible to find a relevant molecular weight for each peak and to propose an estimated chemical structure.

Thus, drastic difference in composition between undifferentiated cell cultures and leaves extracts was noted. None of the known toxic cardiac glycosides described in Calotropis gigantea or *Calotropis procera* were amongs the most abondant compounds of the undifferentiated cell extract.

2.2.4 Final Ingredient

Both extracts (i.e. ethanol and aqueous), were re-suspended in a support consisted of glycerol 80% and water 20% at a concentration of 0.4%. The final concentration for the ingredient was then fixed at 4% (40 g/L).

The extract used in the examples detailed herein below is an aqueous (100% water) extract in a support media consisted of glycerol 80% (w/w) and water 20% (w/w) at a final concentration of 40 g/L. The extract had a dark amber color. The extract was stored protected from sun light at 4° C. (and for long term storage freeze at −20° C.).

Figure 4:
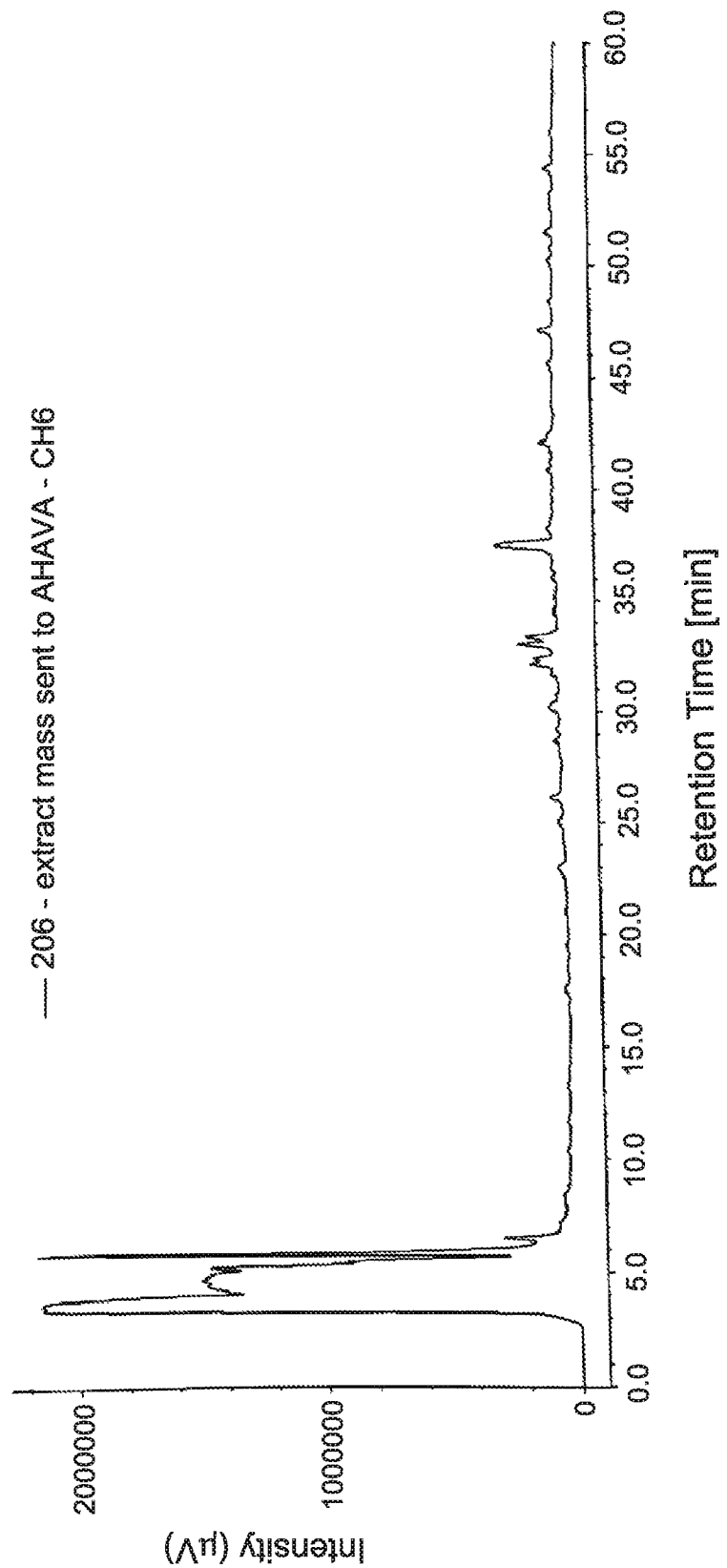
FIG. 4 represents the HPLC analysis of the Apple of Sodom extract according to some embodiments of the invention.

FIG. 4 represents the HPLC analysis of the dry extract used in the examples below. The HPLC was conducted on column Luna C18 250×4.6, 5 μm, injection volume of 20 μl, at a flow rate of 0.7 ml/min and detection at 220 nm. The solvents used were ultrapure water+0.01% phosphoric acid (A) and acetonitrile (ACN)+0.01% phosphoric acid (C) (85% A and 15% C at times 0 and 10, 80% A and 20% C at times 20 and 60.

Unless otherwise note, the percentages of the AoS extract in the compositions of the present disclosure are provided herein above and below in g/L (weight per volume) i.e., the weight in grams of the AoS extract in 1 liter total volume of the composition.

It is noted that the AoS extract was tested for biological activity on ex-vivo human skin models (See below). Different extract dilutions at concentrations from 4 g/L to 8 mg/ml were tested for safety. All of them did not show decrease in vitality parameters (data not shown).

Example 3: Biological Activity Studies of AoS Aqueous Extract and Dead Sea Minerals

3.1. Anti-Inflammatory and Anti-Irritation Properties Evaluation of AoS Extract and Osmoter™

The objective of the current study was to evaluate the anti-inflammatory and anti-irritant capacities of aqueous AoS extract (referred to herein in Table 3 and Table 4 as "Test item 2") on human skin explants (ex vivo) in combination with AHAVA's commercial Dead Sea extract, Osmoter™.

Tested Skin Model:
Ex vivo human skin organ culture (HOSC) was used as a representative skin laboratory model for all biological experiments.

Human skin cultures were obtained from healthy female (age 23-45) undergoing abdominal plastic surgery. The study was initiated at the day of surgery. Fixed size of explant skin pieces (0.64 cm²) were cut from the skin tissue, using a designated press apparatus. The skin pieces were laid in culture medium (DMEM supplemented with 100 U/ml penicillin and 100 μg/ml streptomycin), dermal side down in the medium and epidermis up. The pieces were incubated overnight at 37° C. with 5% $CO_2$ for recovery for 24 hr.

Tested Treatments:
The aqueous AoS extract's stock was at a concentration of 40 g/L (w/v) with a support consisted of glycerol 80% and water 20%.

Aos aqueous extract, Osmoter™ and their combinations were tested in two experimental models for inflammation and irritation.

Each treatment was carried out in triplicates. Each well contained two skin pieces.

Tested Biomarkers:
The anti-inflammatory and anti-irritation properties were tested by viability, cytokine induction (TNFα, IL-1a and IL-1β), Prostaglandin 2 ($PGE_2$) synthesis and of matrix metalo-proteinase (MMP) activation.

Cytokines quantification of skin culture supernatants was analyzed by using specific ELISA kits for TNFα, IL-1a, and IL-1β. Calibration curves were generated in duplicates. Each sample was tested in duplicates.

Prostaglandin $E_2$ biosynthesis was determined using appropriate ELISA kit, according to manufacturer instructions. Calibration curve was generated in duplicates. Each sample was tested in duplicates.

3.1.1 Anti-Inflammatory Properties Evaluation of AoS and Osmoter™

Inflammation characteristics were induced by fresh culture medium with LPS (Lipo Poly Saccharide, 10 μg/ml), as detailed herein above. The different treatments are described in Table 3 (totally 26 treatment groups, wherein in groups 1-13 no inflammation was induced and wherein in groups 14-26 inflammation was induced by LPS). Culture medium without supplements was used as negative, unstimulated control (Group 1). In addition, glycerol:DDW (80:20) mixture was used as vehicle control group (Group 2).

The dilutions of the Test item 2 (AoS aqueous extract) samples were carried out in its original formulation i.e., Glycerol:DDW (80%:20%) mixture. Naïve and LPS-stimulated cultures were treated without or with three concentrations of the AoS extract by applying them on the epidermis topically (3 μl). The positive control (Group 14) contained LPS, without addition of other agents.

Concomitantly, the Osmoter™ was applied topically to the skin explants (Groups 6-13, 19-26). When applied with the plant extract or vehicle, the Osmoter™ was pre-diluted in Glycerol:DDW (80%:20%) mixture. Thus, the vehicle volume was fixed (3 μl).

The pieces were incubated for 48 hr at 37° C. with 5% $CO_2$. Each treatment was carried out in triplicates. Each well contained two skin pieces.

At the end of all incubations, the epidermis was peeled and its viability was measured by the 5-dimethylthiazol-2-yl]-2,5-diphenyl tetrazolium bromide (MTT) assay.

The spent medium from treated skin cultures were collected frozen at −70° C.

Cytokines quantification of skin culture supernatants were analyzed by using specific ELISA kits for TNFα and IL-1β. Calibration curves were generated in duplicates. Each sample was tested in duplicates.

$PGE_2$ biosynthesis and MMP-2 levels were determined using appropriate ELISA kits, according to manufacturer instructions. Calibration curves were generated in duplicates. Each sample was tested in duplicates.

TABLE 3

Treatment groups - inflammation*

| # | Description | Inflammation | Concentration |
|---|---|---|---|
| 1. | Naïve cells | N/A | N/A |
| 2. | Vehicle control | | N/A |
| 3. | Test item 2 (extract) | | 0.2 g/L |
| 4. | Test item 2 (extract) | | 0.4 g/L |
| 5. | Test item 2 (extract) | | 0.8 g/L |
| 6. | Osmoter | | 0.5% |
| 7. | Osmoter | | 0.1% |
| 8. | Test item 2 + Osmoter | | 0.2 g/L/0.1% |
| 9. | Test item 2 + Osmoter | | 0.2 g/L/0.5% |
| 10. | Test item 2 + Osmoter | | 0.4 g/L/0.1% |
| 11. | Test item 2 + Osmoter | | 0.4 g/L/0.5% |
| 12. | Test item 2 + Osmoter | | 0.8 g/L/0.1% |
| 13. | Test item 2 + Osmoter | | 0.8 g/L/0.5% |
| 14. | Stimulated control | LPS | N/A |
| 15. | Vehicle control | | N/A |
| 16. | Test item 2 (extract) | | 0.2 g/L |
| 17. | Test item 2 (extract) | | 0.4 g/L |
| 18. | Test item 2 (extract) | | 0.8 g/L |
| 19. | Osmoter | | 0.5% |
| 20. | Osmoter | | 0.1% |
| 21. | Test item 2 + Osmoter | | 0.2 g/L/0.1% |
| 22. | Test item 2 + Osmoter | | 0.2 g/L/0.5% |
| 23. | Test item 2 + Osmoter | | 0.4 g/L/0.1% |
| 24. | Test item 2 + Osmoter | | 0.4 g/L/0.5% |
| 25. | Test item 2 + Osmoter | | 0.8 g/L/0.1% |
| 26. | Test item 2 + Osmoter | | 0.8 g/L/0.5% |

*Test item 2 refers to an aqueous AoS extract in 80% glycerol;
N/A = not applicable Results FIGS. 5A-5C illustrate the impact of Osmoter™, Apple of Sodom extract and their combinations on LPS-induced inflammation. As noted above, the HSOC pieces were incubated with LPS to induce inflammation. Concomitantly, the explants were treated without or with the indicated concentrations for 48 hr. Then, epidermis viability was measured by MTT assay (FIG. 5A). In addition, IL-1β. (FIG. 5B) and TNFα (FIG. 5C) levels in the spent medium were evaluated by ELISA. Cytokine results are provided in ng/ml. Mean±SEM; n=5. *p<0.05 for differences from the vehicle control. #p<0.05 for differences from the LPS-treated control. As expected, a mild compensatory increase in the MTT values are shown in the LPS-stimulated groups (FIG. 5A). Of note, the different compounds and combinations did not modulate the skin viability, indicating that the concentration selection was in the non-toxic therapeutically window. As per the levels of IL-1β and TNFα. LPS treatment increased IL-1β and TNFα levels significantly (FIG. 5B and FIG. 5C, respectively). It is noted that Aos aqueous extract have reduced both inflammation markers. In addition, the Osmoter™ attenuated IL-1β level at 0.1%, but not those of TNFα. The results indicate that in the studied system, AoS aqueous extract and the Osmoter™ are compatible in the lower concentration levels. However, no additive impact of these two active components was observed.

The same concentrations and experimental design were used to evaluate the impact of the Test items on MMP2 and $PGE_2$. Also, to evaluate the system reproducibility and to monitor known parameters of LPS-induced inflammation, skin viability and the secretion levels of IL-1β were also determined.

FIGS. 6A-6D also illustrate the impact of Osmoter™, Apple of Sodom extract and their combinations on LPS-induced inflammation. As noted above the HSOC pieces were incubated with LPS to induce inflammation. Concomitantly, the explants were treated without or with the indicated concentrations for 48 hr. Then, epidermis viability was measured by MTT assay (FIG. 6A). In addition, IL-1β (FIG. 6B), $PGE_2$ (FIG. 6C) and MMP2 (FIG. 6D) levels in the spent medium were evaluated by ELISA. Markers results are provided in ng/ml. Mean±SEM; n=3-5. *p<0.05 for differences from the vehicle control. #p<0.05 for differences from the LPS-treated control. FIG. 6A and FIG. 6B show that similar stimulatory results were observed by LPS. Notably, more impressive impact of the test item was observed in attenuating IL-1β levels. As expected, LPS treatment increased $PGE_2$ levels (FIG. 6C). However, no significant reduction was observed in the treated groups, indicating that this stimulatory pathway is not a target of the AoS extract. Although not all extract concentrations inhibited significantly $PGE_2$ secretion, it seems that the 0.2g/L AoS extract as standalone and with 0.5% Osmoter have inhibition effect.

MMP2 (FIG. 6D) was only modulated mildly by the LPS stimuli, thus the tendency of the tested items to attenuate its levels were not significant.

3.1.2 Anti-Irritation Properties Evaluation of AoS and Osmoter™

To induce irritation, 10% SDS was applied topically (3 μl). 15 min later, the cultures were treated with AoS aqueous extract as described in Table 4. Concomitantly, the Osmoter™ was applied topically to the skin explants (Groups 6-13, 19-26). When applied with the plant extract or vehicle, the Osmoter™ was pre-diluted in Glycerol:DDW (80%:20%) mixture. Thus, the vehicle volume was fixed (3 μl).

The dilutions of the Test item 2 samples were carried out in their original formulation—i.e., Glycerol:DDW (80%: 20%) mixture. Fresh skin culture medium in the absence of the two extracts was used as negative, baseline control (Group 1). In addition, glycerol:DDW (80:20) mixture was used as vehicle control group (Group 2). The stimulation control (Group 14) treated with SDS, without additional treatment agent.

The pieces were incubated for 24 hr at 37° C. with 5% $CO_2$. Each treatment was carried out in triplicates. Each well contained two skin pieces (3 well*2 pieces per each group).

After incubation, spent medium from treated skin cultures were collected and frozen at −70° C.

The viability of the epidermis was measured in all the skin pieces by MTT assay. Cytokines quantification of skin culture supernatants were analyzed with specific ELISA kits for TNFα and IL-1α. MMP-2 quantification in skin culture supernatants was analyzed by using specific ELISA kit.

TABLE 4

Treatment groups - skin irritation

| # | Description | Irritation | Concentration |
|---|---|---|---|
| 1. | Naïve cells | N/A | N/A |
| 2. | Vehicle control | | N/A |
| 3. | Test item 2 (extract) | | 0.2 g/L |
| 4. | Test item 2 (extract) | | 0.4 g/L |
| 5. | Test item 2 (extract) | | 0.8 g/L |
| 6. | Osmoter | | 0.5% |
| 7. | Osmoter | | 0.1% |
| 8. | Test item 2 + Osmoter | | 0.2 g/L/0.1% |
| 9. | Test item 2 + Osmoter | | 0.2 g/L/0.5% |
| 10. | Test item 2 + Osmoter | | 0.4 g/L/0.1% |
| 11. | Test item 2 + Osmoter | | 0.4 g/L/0.5% |
| 12. | Test item 2 + Osmoter | | 0.8 g/L/0.1% |
| 13. | Test item 2 + Osmoter | | 0.8 g/L/0.5% |
| 14. | Stimulated control | SDS | N/A |
| 15. | Vehicle control | | N/A |
| 16. | Test item 2 (extract) | | 0.2 g/L |
| 17. | Test item 2 (extract) | | 0.4 g/L |
| 18. | Test item 2 (extract) | | 0.8 g/L |
| 19. | Osmoter | | 0.5% |
| 20. | Osmoter | | 0.1% |
| 21. | Test item 2 + Osmoter | | 0.2 g/L/0.1% |
| 22. | Test item 2 + Osmoter | | 0.2 g/L/0.5% |
| 23. | Test item 2 + Osmoter | | 0.4 g/L/0.1% |
| 24. | Test item 2 + Osmoter | | 0.4 g/L/0.5% |
| 25. | Test item 2 + Osmoter | | 0.8 g/L/0.1% |
| 26. | Test item 2 + Osmoter | | 0.8 g/L/0.5% |

*Test item 2 refers to an aqueous AoS extract in 80% glycerol;
N/A = not applicable Results FIGS. 7A-7C illustrate the impact of Osmoter™, Apple of Sodom extract and their combinations on SDS-induced irritation. As noted above, the HSOC pieces were incubated with SDS to induce irritation. Concomitantly, the explants were treated without or with the indicated concentrations for 48 hr. Then, epidermis viability was measured by MTT assay (FIG. 7A). In addition, IL-1α (FIG. 7B) and TNFα (FIG. 7C) levels in the spent medium were evaluated by ELISA. Cytokine results are provided in ng/ml. Mean±SEM; n=5. *$p<0.05$ for differences from the vehicle control. #$p<0.05$ for differences from the SDS-treated control. FIG. 7A illustrates the changes in epidermis viability. As anticipated, a 40% reduction was observed by the topical application of SDS. Concomitantly, both levels of IL-1α and TNFα (FIG. 7B and FIG. 7C, respectively) were significantly increased by the stimuli. Importantly, both Test items (i.e., AoS aqueous extract as well as the Osmoter™) were able to attenuate this hypersecretion and the reduction in viability. The combination of both Test items was compatible, but not additive.

The same concentrations and experimental design were used to evaluate the impact of the Test item on MMP2 and $PGE_2$. To evaluate the system reproducibility and to monitor known parameter of SDS-induced irritation, skin viability and the secretion levels of IL-1α were measured.

FIGS. 8A-8D also illustrate the impact of Osmoter™, Apple of Sodom extract and their combinations on SDS-induced irritation. As noted above, the HSOC pieces were incubated with SDS to induce irritation. Concomitantly, the explants were treated without or with the indicated concentrations for 48 hr. Then, epidermis viability was measured by MTT assay (FIG. 8A). In addition, IL-1α (FIG. 8B), $PGE_2$ (FIG. 8C) and MMP2 (FIG. 8D) levels in the spent medium were evaluated by ELISA. Markers results are provided in ng/ml. Mean±SEM; n=3-5. #$p<0.05$ for differences from the LPS-treated control.

FIGS. 8A-8D show that similar stimulatory results were observed by SDS. However, due to the inherent changes between human skin donors, it seems that the SDS irritation was more aggressive. Thus, the ameliorating impact of the Test item on IL-1α was reduced.

As seen in the previous experimental system, MMP2 was not highly affected by the irritation. However, $PGE_2$ was significantly increased.

Importantly, in this system, several concentrations of the AoS aqueous extract, Osmoter™ and their combinations were able to reduce the generation of $PGE_2$.

Example 4: Gene Analysis Results of AoS Extract and Osmoter™

The following three samples (test materials) were tested (Control=water)
1. 0.4 g/L (1% of the 40 g/L stock extract) AoS extract vs Control
2. 0.5% (5 g/L) Osmoter vs Control
3. 0.4 g/L AoS extract+0.5% Osmoter vs. Control Treatment Protocol:

The tested skin samples were pre-incubated with the test materials for 24 hours, followed by collection of RNA from the tissues and conduction of DNA micro-array.

Methods

Treatment

MatTek EFT-400 full thickness skin tissues were used as the model for this study. Upon arrival, the full thickness tissues were placed into 6 wells plates with 2 ml of culture media and incubated overnight at 37±2° C. and 5±1% $CO_2$. After this overnight incubation the culture media was replaced with 4 ml of fresh media and the tissues were treated topically with the test materials.

After the application of the test materials the tissues were incubated at 37±2° C. and 5±1% $CO_2$ for 48 hours.

Total RNA Isolation (Ambion RNAqueous Kit)

At the end of the treatment period, the tissues were rinsed and transferred to a 2 ml centrifuge tube containing 700 µl of lysis buffer and homogenized. After centrifuging at 14,000×g for 10 minutes at 4° C. the supernatant from each tube was transferred to a new 1.5 ml tube and mixed with equal volume of 64% ethanol. After mixing the solutions was transferred to glass fiber filter cartridges and the cartridges were loaded into a 1.5 ml collection tube centrifuged for 1 minute at 14,000 RPM in a Napco 2002 Microcentrifuge with a DA-6T fixed angle rotor. The flow through was discarded and any remaining mixture was loaded into the filter cartridge and the centrifugation process was repeated until all of the mixture hadbeen processed. The filter was then washed to remove any residual cellular debris from the RNA bound to the glass fibers by subsequently applying 700 µl of wash solution 1 (1 time) and 500 µl of wash solution 2 (2 times) to the filter cartridge and centrifuging at 14,000 RPM for 1 minute to pass each wash through the cartridge. After each wash, the flow through was discarded. After the final wash one final spin was performed without wash solution to remove any residual wash solution in the filter cartridge. The RNA bound to the glass fibers within the cartridge was then eluted by applying 40 µl of TE buffer (10 mM Tris-HCl, 1 mM EDTA, preheated to 70-80° C.) to the cartridge and centrifuging the cartridge in a new collection tube at 14,000 RPM for one minute. The elution process was then repeated a second time using 20 µl of TE buffer.

mRNA Amplification (Ambion MessageAmp aRNA Kit)

First Strand cDNA Synthesis: To start the first strand synthesis, 10 µl of total RNA for each sample was added to a 600 µl PCR tube and the total volume of liquid in the tube was adjusted to 11 µl with DEPC $H_2O$. Next, 1 µl of T7 Oligo(dT) primer was added and the tube was incubated in a water bath at 70±2° C. for 10 minutes to denature the RNA and then placed on ice to allow the primers to anneal to the poly A ends of the mRNA. After cooling 2 µl of 10× first strand buffer, 1 µl of RNAse inhibitor and 4 µl of dNTP mix were added to each tube, and the tube was incubated at 42° C. in a hybridization oven (Labnet Problot). As soon as the tube was heated, 1 µl of Reverse Transcriptase was added and the tubes were returned to 42±2° C. for 2 hours. At the end of the two hours the tubes were briefly centrifuged to collect all of the fluid at the bottom of the tube and then placed on ice.

Second Strand Synthesis and cDNA Purification: For the synthesis of the second strand of cDNA the following items were added to the tubes above (in the following order): 63 µl DEPC $H_2O$, 10 µl 10× second strand buffer, 4 µl dNTP mix, 2 µl DNA Polymerase and 1 µl of RNAse H. The tubes were mixed and then incubated at 16±2° C. for 2 hours in a refrigerated centrifuge chamber (Precision Durafuge 300R with the rotor removed). Towards the end of the 2 hour incubation a sufficient quantity of DEPC $H_2O$ was warmed to 50±2° C. in a waterbath and a cDNA purification filter cartridge was equilibrated with 50 µl of cDNA binding buffer (one cartridge per sample) for at least 5 minutes. After the samples finished incubating 250 µl of cDNA binding buffer was added to each tube and thoroughly mixed. The contents of the PCR tube were then transferred to the cDNA purification filter cartridge. The cartridge was then placed in a collection tube and centrifuged at 10,000 RPM for 1 minute. The flow-through was discarded and 650 µl of cDNA wash solution was added to the cartridge. The cartridge was centrifuged again and the flow-through was discarded, and then centrifuged one last time to ensure that the wash buffer had been completely emptied from the filter. The cDNA was eluted by applying 10 µl of preheated DEPC $H_2O$ to the filter and centrifuging the filter in a new collection tube at 10,000 RPM for one minute. This elution was performed one additional time to give a total volume of 16-18 µl of recovered cDNA solution.

In Vitro Transcription to Synthesize aRNA and aRNA Purification: The in vitro transcription began by adding the following to the cDNA solutionprepared above: 4 µl each of T7 ATP solution, T7 CTP solution, T7 GTP solution, T7 UTP solution, 4 µl of 10× Reaction buffer, and 4 µl of T7 enzyme mix. The tube was mixed and then incubated at 37±2° C. for 6-14 hours in a hybridization oven. Towards the end of the incubation a sufficient volume of Elution Solution was warmed to 50-60° C. and an aRNA filter cartridge was equilibrated with 100 µl of aRNA binding buffer for at least 5 minutes. At the end of the incubation period, 350 µl of aRNA binding buffer was added to the sample tubes and thoroughly mixed. An additional 250 µl of absolute ethanol was also added to each tube. The mixture was then transferred to an aRNA filter cartridge; the cartridge was inserted into a collection tube and centrifuged at 10,000 RPM for 1 minute. The flow-through was discarded and 650 µl of aRNA wash buffer was added to the cartridge followed by centrifuging at 10,000 RPM for one minute. After discarding the flow through the cartridge was spun one final time to remove all traces of the wash buffer. The cartridge was then transferred to a new collection tube and 40 µl of prewarmed Elution Solution was added to the cartridge. The cartridge was incubated for 2 minutes at room temperature and then the aRNA was eluted by centrifuging for 1 minute at 10,000 RPM. This elution was performed one additional time to give a total volume of 80 µl of aRNA solution. The final concentration of the aRNA was determined by the Ribogreen assay described above. In addition, the quality of the aRNA was checked via gel electrophoresis as described below.

RNA Concentration Assay (Molecular Probes Ribogreen Assay)

The Ribogreen reagent is provided as a stock solution in DMSO. Prior to use the reagent was diluted 2000 fold in TE buffer. The RNA assay requires 200 µl of diluted Ribogreen reagent per sample to be tested and 1 ml of the reagent for the standards. A series of RNA standards was prepared by diluting purified ribosomal RNA derived from E. coli to the following concentrations: 1 µg/ml, 0.5 µg/ml, 0.1 µg/ml, 20 ng/ml and 0 ng/ml (blank). Prior to assaying, one microliter of the RNA samples prepared above was diluted 1000 fold in TE buffer. For the RNA assay, 100 µl of the diluted samples or standards was transferred to the wells of a black 96-well plate. The samples and standards were assayed in duplicate. After the samples/standards were added to the plate 100 µl of the diluted Ribogreen assay reagent was added and the plate was gently mixed and allowed to incubate for 5-10 minutes protected from the light. After this incubation the plate was read with a Thermo Labsystems Fluorskan Ascent FL fluorometer using an excitation wavelength of 500 nm and an emission wavelength of 525 nm.

Labeling of aRNA with Fluorescent Dyes (PerkinElmer ASAP RNA Labeling Kit)

Two tubes were prepared for the labeling process, one for Cy3 labeling (green) and one for Cy5 labeling (red). To the Cy3 tube 2 µg of aRNA prepared from the untreated/control sample (the actual color assignment for each sample is not important, but for consistency we normally use Cy3 for the untreated sample) and enough DEPC $H_2O$ was added to bring the total volume up to 4 µl. To the Cy5 tube 2 µg of aRNA prepared from the sample treated with the test material and enough DEPC H$_2$O was added to bring the total volume up to 4 µl. To both tubes 5 µl of ASAP labeling buffer was added along with 1 µl of the specific dye for the tube (Cy3 or Cy5). The tubes were incubated for 15 minutes at 85±2° C. At the end of the 15 minutes the tubes were placed on ice to cool them and then add 2.5 µl of ASAP stop solution was added to each tube.

Purification of Labeled aRNA

To purify the labeled aRNA, a Millipore Microcon YM-30 filter column was inserted into a collection tube and filled with 400µl of TE buffer. The Cy3 and Cy5 probes were combined (6 µl of each or approximately 1 µg of each labeled aRNA) and then added to the microcon filter and thoroughly mixed with the TE buffer. The filter was centrifuged at 12,000 RPM for 8 minutes and the flow through was discarded. The column was then washed twice with 400 µl of TE buffer, discarding the flow though after each centrifugation (12,000 RPM for 8 minutes). After the final wash the filter column was inverted, placed into a new collection tube and centrifuged at 12,000 RPM for 2 minutes to collect the probe (the probe was concentrated in a volume of 2-30 ul of residual TE buffer).

Microarray Hybridization and Washing (Agilent Technologies Microarrays)

For hybridization, 11 µl of 10× control target RNA (supplied with Agilent Technologies In Situ Hybridization Kit) was mixed with 30 µl of DEPC water and 2.5 µl of 25× Agilent Fragmentation Buffer. This mixture was allowed to incubate at 65° C. for approximately 30 minutes in a hybridization oven. At the end of the incubation 55 µl of Agilent Hybridization Buffer was added along with the fluorescent aRNA probes prepared above. An Agilent SUREHYB hybridization chamber was prepared by inserting a glass gasket slide into the bottom half of the chamber and the hybridization mixture (approximately 110 µl) was applied to the glass gasket slide and a custom Agilent DNA Microarray Chip was placed face down on top of this gasket such that the hybridization solution was sandwiched between the glass gasket slide and the microarray face of the chip. The top half of the chamber was then attached and the connecting thumbscrew was tighted. After verifying that there was good bubble formation in the chamber, it was placed into the hybridization oven for approximately 17 hours (65° C. and rotating at 4 RPM). At the end of the hybridization period the microarrays/glass gasket were removed from the SUREHYB chamber and placed in 50 ml of wash solution 1 (room temperature, 6× SSC, 0.005% Triton X-102). After the gasket had fallen away from the microarray, the array was placed in 300 ml of fresh wash solution 1 on a magnetic stir plate. The array was washed while the solution was mixed at medium speed for 10 mintues and then transferred to 300 ml of wash solution 2 (0.1× SSX, 0.005% Triton X-102, 4° C.) for 5 minutes. After the final wash the array was dried by centrifuging at 500 RPM for 5 minutes.

Microarray Scanning and Analysis

The microarrays were scanned with an Axon GenePix 4100A Scanner with the scanning resolution set to 5 µm and analyzed with GenePix Pro software. During the initial scan the PMT gains for the scanner were adjusted such that the cy5/cy3 image count ratios were between 0.95 and 1.05.

Calculations

Microarray Calculations

Fluorescence intensities for the microarrays were subjected to global normalization. The total fluorescent signal for both dyes were normalized to one to establish a correction factor that would make the total intensities for both dyes equal. Criteria for evaluating changes in gene expression will vary from study to study however typically three criteria are required:

1. The ratio of Cy3/Cy5 (treated/untreated) fluorescence intensity is greater than 1.3 or less than 0.66. This relates to a change in gene expression of at least +/−30%.
2. The fluorescence intensity of the gene marker is greater than the background intensity.

Advanced Analysis of the Microarray Data

The advanced analysis reported here is based on the results of the microarray data detailed herein above.

Since no replicates were used the only value that was available for the advance analysis is the gene adjusted logFCs (a known bioinformatics calculation method) of the three comparisons.

Gene Set Enrichment Analysis (GSEA):

GSEA (Subramanian et at., PNAS 2005) [18] use complete expression data (cut-off independent) to determine whether a-priori defined sets of genes show statistically significant, concordant differences between two biological states. In this analysis, for each comparison, the adjusted logFCs were used for ranking the whole transcriptome. Gene sets of the MSigDB database category H were examined (MsigDB v6.1, May 2017 release) [19].

The effects of Osmoter™, Apple of Sodom extract and their combination were analyzed by the GSEA approach (data not shown).

Table 5 provides a list of twenty biological pathways and data regarding down (represented by *) and up (represented by **) regulated gene sets (FDR<0.05) in untreated samples versus samples which were treatment with AoS extract, Osmoter™ and their combination.

In up-regulated gene-set the up-regulated genes are enriched, compared to down-regulated genes that are enriched in the down-regulated gene-set in Table 5.

TABLE 5

Down (represented by *) and Up (represented by **) regulated gene sets (FDR < 0.05) in untreated samples versus treatment with AoS, Osmoter ™ (Osm) and their combination.

| Pathway | Down AoS | Up AoS | Down Osm | Up Osm | Down AoS + Osm | Up Aos + Osm |
|---|---|---|---|---|---|---|
| ADIPOGENESIS | | | | 1 ** | | 1 ** |
| ANDROGEN_RESPONSE | | | | | | 1 ** |
| APOPTOSIS | | | | | | 1 ** |
| COMPLEMENT | 1 * | | 1 * | | | |
| DNA REPAIR | | | | 1 ** | | 1 ** |
| EPITHELIAL_MESENCHYMAL_TRANSITION | 1 * | | | | | 1 ** |
| ESTROGEN_RESPONSE_EARLY | | | 1 * | | | |

TABLE 5-continued

Down (represented by *) and Up (represented by **) regulated gene sets (FDR < 0.05)
in untreated samples versus treatment with AoS, Osmoter™ (Osm) and their combination.

| Pathway | Down AoS | Up AoS | Down Osm | Up Osm | Down AoS + Osm | Up AoS + Osm |
|---|---|---|---|---|---|---|
| ESTROGEN_RESPONSE_LATE | | | 1 * | | | |
| GLYCOLYSIS | 1 * | | | | | 1 ** |
| HEME_METABOLISM | | | | | | 1 ** |
| HYPOXIA | 1 * | | 1 * | | | 1 ** |
| INTERFERON_ALPHA_RESPONSE | 1 * | | | | | |
| INTERFERON_GAMMA_RESPONSE | 1 * | | 1 * | | | |
| MTORC1_SIGNALING | 1 * | | 1 * | | | 1 ** |
| MYC_TARGETS_V1 | | | | | | 1 ** |
| OXIDATIVE_PHOSPHORYLATION | | | | 1 ** | | 1 ** |
| P53_PATHWAY | | | 1 * | | | |
| PROTEIN_SECRETION | | | | | | 1 ** |
| TNFA_SIGNALING_VIA_NFKB | | | 1 * | | | 1 ** |
| UNFOLDED_PROTEIN_RESPONSE | 1 * | | 1 * | | | |

Table 5 above illustrates that in some biological pathways (shown bold, See left column of Table 5) the combination of the AoS extract and the Osmoter surprisingly changed the down regulation observation of the individual active ingredient to an up regulation. For example, in the epithelial mesenchymal transition pathway the down regulation observed with the AoS extract was changed to an up regulation in the case of the combination of AoS and Osmoter. The same trend was observed with the glycolysis pathway. In the hypoxia pathway the down regulation observed with the individual extracts i.e., Osmoter and AoS changed to an up regulation in the case of the combination of the two extracts. The same observation was detected with the MTORC1 signaling pathway. In the TNFA signaling via NFKB pathway, the down regulation observed with the Osmoter changed to an up regulation in the case of the combination of the two extracts. This observed action of the combination of the present invention is surprising and unexpected.

The data provided herein above in Table 5 implies that the combination of the Osmoter and the AoS extract may be used for selective treatment and/or prevention of specific one or more disorders which are related to specific biological pathways. The concentrations of each of the extracts in the combination may be optimized in order to achieve selective activity e.g., affecting specific one or more pathways while not affecting (or affecting to less extent) other one or more pathway/s.

Example 5: Protein Analysis Results of AoS Extract and Osmoter™

A biological study at the protein level was conducted. The study focused on the following three biological pathways in which an unexpected effect was observed with respect thereto at the gene expression level i.e., Glycolysis, Hypoxia and Epithelial Mesenchymal Transition (See Example 4 above).

For the three aforementioned pathways, representative protein/enzymatic biomarkers were selected as follows:
Glycolysis
phosphofructokinase (PFK)
Hypoxia
Hypoxia Inducible Factor 1 (HIF1)
Epithelial Mesenchymal Transition
Fibronectin (FBN)

Detailed description of the experiments and the results thereof are provided herein below.

The MatTek Full thickness skin tissue model was used to assess the ability of the test materials to alter the expression of phosphofructokinase (PFK) and hypoxia inducible factor 1 (HIF1). This study also assessed the ability of the test materials to affect the production of fibronectin (FBN).

The following three samples (test materials) were tested:
1. 1% Calatrois Procea (AoS) extract (brown, clear liquid) (it is noted that this test sample was prepared from a stock solution of 40 g/L AoS extract i.e., resulting with a final concentration of 0.4 g/L).
2. 0.5% Osmoter (colorless, clear liquid)
3. 1% Calatrois Procea (AoS) extract+0.5% Osmoter (it is noted that this test sample was prepared from a stock solution of 40 g/L AoS extract i.e., resulting with a final concentration of 0.4 g/L)

Summary of Test Methods

In this study MatTek full thickness skin tissues were topically treated for 48 hours with the test materials. At the end of the 48-hour treatment period the tissues were rinsed to remove the test material and then homogenized. The tissue homogenates were used to measure the expression of PFK and HIF1 using immunoblotting techniques. The media for the cultured tissues was collected and used to measure fibronectin production via an ELISA based method.

Methods

Tissue Preparation

Upon arrival, the MatTek Full Thickness Tissues were stored at 4° C. until used. Prior to use, the tissues to be used were removed from the agarose-shipping tray and placed into a 6-well plate containing 2.5 ml of assay medium (37±2° C.). The tissues were then incubated overnight at 37±2° C. and 5±1% $CO_2$. After this initial overnight incubation, the assay medium was replaced with 5 ml of fresh medium (37±2° C.) and the tissues were treated topically with the test materials for 48 hours. At the end of the incubation period the surface of the tissues were rinsed with PBS to remove the test materials, after which the tissues were homogenized and the tissue culture media was collected.

Tissue Homogenization and Protein Assay

Individual full thickness tissues were placed into a 2 ml centrifuge tube containing 500 μl of CelLytic MT Cell Lysis Reagent (supplemented with protease inhibitors) and homogenized with a PRO200 homogenizer. The homogenized tissues were then centrifuged at 12,000×g for 10 minutes at 4° C. to pellet any insoluble cellular debris. The supernatant was then transferred to a fresh 1.5 ml centrifuge tube and assayed for protein concentration using a BCA protein assay. Tissue homogenate samples were then prepared in PBS such that 10 μg of protein was combined with 150 μl of PBS.

Blotting and Immunodetection

A nitrocellulose membrane was equilibrated in phosphate buffered saline (PBS) and assembled into a Bio-Dot microfiltration apparatus. After assembly, 200 μl of PBS was added to each well used in the Bio-Dot and the vacuum was applied to ensure that there was adequate flow through all of the wells. Next, the 10 μg samples of tissue homogenate prepared in 150 μl of PBS were assigned a well in the apparatus and applied to the appropriate well. The samples were filtered under low vacuum. The membrane was then removed from the Bio-Dot apparatus, washed in PBS for 5-10 minutes and then placed into blocking solution (PBS with 1% bovine serum albumin) and allowed to incubate for at least 1 hour at room temperature on a rocking platform.

Antibody Incubation and Detection: PFK, HIF1, GAPDH

After blocking, the membrane was transferred to 20 ml of PBST (PBS with 0.1% Tween-20) and 0.1% bovine serum albumin with an appropriate dilution of antibody and allowed to incubate overnight at 4° C. on a rocking platform. After this incubation the membrane was washed 3 times in PBST (15 minutes per wash). The secondary antibody (conjugated with a fluorophore) was then incubated with the membrane in 15 ml of PBST with 0.1% bovine serum albumin for 1 hour at room temperature and then washed 3 times with PBST (15 minutes per wash).

After the final wash, the membrane was placed into a BioRad Molecular Imager FX and scanned using an excitation laser and emission filter combination appropriate for the fluorophore. Images produced by the scanner were then analyzed using ImageJ image analysis software. In addition to the target protein, each immunoblot was also probed with GAPDH, which was used to normalize the data.

Fibronectin Assay

A series of fibronectin standards was prepared ranging from 0 ng/ml to 800 ng/ml. Next, an ELISA microplate was prepared by removing any unneeded strips from the plate frame followed by the addition of 100 μl of either sample (collected tissue culture media) or standard was then added to appropriate wells and the microplate was covered and allowed to incubate for 1±0.25 hours at 37° C. After the incubation the wells were aspirated and washed three times with 400 μl of wash buffer. After the last wash was removed 100 μl of a peroxidase-labeled anti fibronectin antibody was added to each well used in the assay and the microplate was covered and allowed to incubate for 1±0.25 hours at 37° C. After the incubation the wells were aspirated and washed three times with 400 μl of wash buffer and then 100 μl of peroxidase substrate solution (hydrogen peroxide +tetramethylbenzidine as a chromagen) was added to each well and the plate was incubated for 15±5 minutes at room temperature. After the incubation 100 μl of stop solution (1 N sulfuric acid) was added to each well and the plate was read using a microplate reader at 450 nm.

Calculations

Image Analysis

Fluorescence intensity measurements were expressed in Relative Fluorescence Units (RFU). RFUs for the target protein of interest were then normalized to GAPDH. Mean normalized RFU values for each treatment were then calculated and treatments were compared using a one way ANOVA.

Fibronectin Analysis

For the fibronectin assay the absorbance values for the known standards were used to generate a standard curve. The values for the unknown samples were then determined from this standard curve and means for each treatment was compared using a one way ANOVA.

Results

The results for the PFK and HIF1 immunoblot assays are presented in Tables 6-7 and FIGS. 9-10, respectively. The values for these assays are expressed as a ratio normalized to GAPDH (mean ratio±standard deviation). The results for the fibronectin assay are presented in Table 8 and FIG. 11. These values are expressed as mean concentration (ng/ml) ±standard deviation. For all of the assays, an (*) denotes values that are significantly different from the Untreated tissues ($p<0.05$).

TABLE 6

Phosphofructokinase Assay

| Treatment | Ratio to GAPDH |
|---|---|
| Untreated | 20.03 ± 1.10 |
| 1%* Calatropis Procera | 21.34 ± 0.96 |
| 0.5% Osmoter | 21.21 ± 1.27 |
| 1%* Calatropis Procera + 0.5% Osmoter | 25.12 ± 1.98** |

*1% here refers to a final concentration of 0.4 g/L
**Denotes values which are significantly different from Untreated ($p < 0.05$)

Table 6 illustrates a significant enhancement in PFK expression of about 20% when skin was topically applied with a combination of *Calatropis procera* and Osmoter relative to the untreated skin or when treated separately with each of the tested ingredients alone.

TABLE 7

Hypoxia Induced Factor 1 Assay

| Treatment | Ratio to GAPDH |
|---|---|
| Untreated | 6.39 ± 0.44 |
| 1%* Calatropis Procera | 6.77 ± 0.29 |
| 0.5% Osmoter | 6.15 ± 0.45 |
| 1%* Calatropis Procera + 0.5% Osmoter | 7.54 ± 0.40** |

*1% here refers to a final concentration of 0.4 g/L
**Denotes values which are significantly different from Untreated ($p < 0.05$)

Table 7 illustrates a significant increase expression of HIF1 of about 15% after treatment with a combination of *Calatropis procera* and Osmoter.

TABLE 8

Fibronectin (FBN) Assay

| Treatment | Fibronectin (ng/ml) |
|---|---|
| Untreated | 3591 ± 257 |
| 1%* Calatropis Procera | 4621 ± 401** |
| 0.5% Osmoter | 3916 ± 156 |
| 1%* Calatropis Procera ± 0.5% Osmoter | 4513 ± 332** |

*1% here refers to a final concentration of 0.4 g/L
**Denotes values which are significantly different from Untreated ($p < 0.05$)

Table 8 illustrates that both topical treatment with *Calatropis procera* alone and mixture of *Calatropis procera* and Osmoter significantly increases fibronectin production (about 22% and 20%, respectively).

DISCUSSION

The results for the study are be summarized in Table 9 below:

TABLE 9

Summary of the Results

| Treatment | PFK | HIF1 | FBN |
|---|---|---|---|
| Untreated | — | — | — |
| 1%* *Calatropis Procera* | — | — | √ |
| 0.5% Osmoter | — | — | — |
| 1%* *Calatropis Procera* + 0.5% Osmoter | √ | √ | √ |

*1% here refers to a final concentration of 0.4 g/L

When used individually, only one of the test materials was observed to have an impact on any of the end points. The topical application of the above 1% *Calatropis procera* solution was observed to significantly increase fibronectin production in the tissues. The topical application of the 0.5% Osmoter solution by itself was not observed to have an effect on any of the end points. However, the combination of *Calatropis procera* and the Osmoter was observed to be effective at significantly increasing the expression of phosphofructokinase and hypoxia inducible factor 1.

Hypoxia inducible factor 1 plays a role in many processes in the skin, including wound healing and responding to infections of the skin. In this study the combination of the tested materials was observed to increase the expression of HIF1 suggesting that these materials may play a beneficial role in wound healing and epidermal immune function.

Finally, both the topical treatment with *Calatropis procera* and the combination treatment of *Calatropis procera* and Osmoter were observed to increase fibronectin production. However, the increase in fibronectin production was similar for both the *Calatropis procera* material alone and the combination of *Calatropis procera* and Osmoter. Without wishing to be bound by any theory, this may suggest that in both cases it is probably just the *Calatropis procera* inducing the effect on fibronectin, since the combination treatment did not result in any additional fibronectin production. Yet, the combination of the two materials did not diminish fibronectin production and the benefits of the combination with respect to PFK and HIF1 would suggest that combining the two ingredients provides a better treatment than either material alone.

The experimental data provided in Example 5 support the observations which were detailed in Example 4. The unexpected results which were observed in Example 4 in connection with gene level are illustrated also in the protein level of Example 5. In particular, the effect illustrated in connection with the biological glycolysis and hypoxia pathways at the gene level is also illustrated in the protein level for the representative biomarker.

The invention claimed is:

1. A composition comprising at least one Dead Sea extract and at least one extract of Apple of Sodom, wherein the at least one extract of Apple of Sodom is an Apple of Sodom callus extract, and wherein said composition is a synergistic composition.

2. The composition according to claim 1, wherein said Dead Sea extract is a mixture of natural materials obtained from waters of the Dead Sea, mud surrounding Dead Sea and/or soil bed of Dead Sea.

3. The composition according to claim 1, wherein said Dead Sea extract is saline waters obtained from Dead Sea.

4. The composition according to claim 1, wherein said callus extract is obtained from one or more of Apple of Sodom roots, leaves, leaf blades, seeds, stems, fruits, shoot and barks.

5. The composition according to claim 4, wherein said Apple of Sodom is selected from the group consisting of an ex-vitro plant, an ex-vitro explant, and an in-vitro plantlet.

6. The composition according to claim 1, wherein said at least one extract of Apple of Sodom is a non-toxic extract.

7. The composition according to claim 6, wherein said at least one extract of Apple of Sodom is substantially free of the Calotropin toxin.

8. The composition according to claim 1, wherein said at least one extract of Apple of Sodom is from Apple of Sodom originated from Dead Sea area.

9. The composition according to claim 1, wherein said at least one extract of Apple of Sodom is an aqueous extract.

10. The composition according to claim 1, wherein said at least one extract of Apple of Sodom is a pure extract or an extract formulated with at least one additive.

11. The composition according to claim 1, wherein said composition is for topical application.

12. The composition according to claim 1, being in the form selected from a lotion, an ointment, a gel, a mask, a toner, an essence, a cream, a water in oil or oil in water emulsion, a shampoo, a moisturizer, a sunscreen, a stick, a spray, an aerosol, foam, a paste, a mousse, a solid, semi-solid, or a liquid make-up, a foundation, and an eye make-up.

13. The composition according to claim 1 for use in one or more of: (i) protecting and/or improving state of the skin of a subject; (ii) preventing and/or treating imperfections of the skin of a subject; and (iii) treating or preventing a disease or disorder of the skin of a subject said disease or disorder is associated with one or more of biological pathways selected from epithelial mesenchymal transition cellular pathway, glycolysis cellular pathway and hypoxia cellular pathway.

14. A method of one or more of protecting and/or improving state of the skin of a subject, and preventing and/or treating imperfections of the skin of a subject in need thereof, wherein said method comprising topically administering a composition according to claim 1 onto the skin of said subject.

15. The method according to claim 14, for treating rings under an eye, symptoms of aging, protecting skin, increasing detoxification of xenobiotics, intervening on pigmentation level, inhibiting melanogenesis, protecting body against pollution, stimulating detoxification systems, stimulating hair and body hair growth, modulating DHT levels, intervening on adipocytes, and/or promoting lipolysis.

16. A method for treating or preventing a disease or disorder of the skin of a subject, wherein said method comprising administering to a subject in need thereof a composition according to claim 1 wherein said disease or disorder is skin inflammation and/or skin irritation.

* * * * *